United States Patent [19]

Baumgarth et al.

[11] 4,086,362
[45] Apr. 25, 1978

[54] PROSTENOIC ACID DERIVATIVES

[75] Inventors: Manfred Baumgarth; Hans-Eckart Radunz; Dieter Orth; Reinhard Lissner; Hans-Joachim Enenkel, all of Darmstadt, Germany; Filippus Johannes Zeelen, Heesch, Netherlands

[73] Assignee: Merck Patent Gesellschaft mit beschränkter Haftung, Darmstadt, Germany

[21] Appl. No.: 634,349

[22] Filed: Nov. 24, 1975

[30] Foreign Application Priority Data

Nov. 27, 1974  Germany .......................... 2455976

[51] Int. Cl.² .................. C07C 177/00; A61K 31/19;
A61K 31/215
[52] U.S. Cl. .............................. 424/305; 260/514 D;
260/520 C; 542/426; 542/429; 424/308;
424/317; 560/61; 560/62; 560/121; 560/231;
560/255
[58] Field of Search ...................... 260/468 D, 514 D;
424/305, 308

[56] References Cited
PUBLICATIONS

Chem. Abstracts 76, Index Guide, 131, (1972).

Primary Examiner—Robert Gerstl
Attorney, Agent, or Firm—Millen & White

[57] ABSTRACT

Prostenoic acid derivatives of the general formula

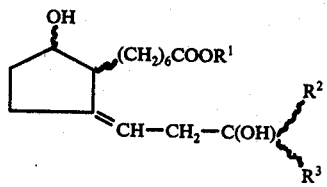

wherein
$R^1$ is H or alkyl or 1–4 carbon atoms;
$R^2$ is alkyl of 5 – 9 carbon atoms, phenoxymethyl or phenoxymethyl substituted by up to 3 of F, Cl, Br, $CH_3$, $CF_3$, or $OCH_3$;
$R^3$ is H or alkyl or 1 – 5 carbon atoms, and physiologically acceptable salts thereof, as well as intermediates therefore are blood-pressure lowering, vasodilatory, diuretic and nasal mucosa decongesting agents.

52 Claims, No Drawings

PROSTENOIC ACID DERIVATIVES

BACKGROUND OF THE INVENTION

This invention relates to novel pharmacologically active prostenoic acid derivatives in the form of racemates and optically-active enantiomers and the preparation thereof.

SUMMARY OF THE INVENTION

In one composition aspect, this invention relates to prostenoic acid compounds of Formula I

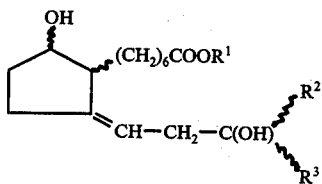

wherein
$R^1$ is H or alkyl of 1 to 4 carbon atoms;
$R^2$ is alkyl of 5 to 9 carbon atoms, phenoxymethyl or phenoxymethyl substituted by up to 3 of F, Cl, Br, $CH_3$, $CF_3$ or $OCH_3$;
$R^3$ is H or alkyl of 1 to 5 carbon atoms; and physiologically acceptable salts thereof.

In other composition aspects, this invention relates to intermediates for the production of compounds of Formula I and to pharmaceutical compositions comprising a compound of Formula I or a physiologically acceptable salt thereof.

In process aspects, this invention relates to processes for the production of the novel compounds of this invention and for the use of the compounds of Formula I and their physiologically acceptable salts.

In another aspect, this invention relates to prostenoic acid derivatives of the Formula II

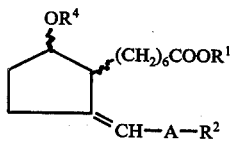

wherein
A is $CH_2D$ or $CH=C(OR^5)$;
$R^4$ is H or $R^5$;
D is a free or ketalized carbonyl group;
$R^5$ is acyl of up to 4 carbon atoms; and
$R^1$ and $R^2$ are as above,
and their metal salts and ammonium salts, also have pharmacological activity and are valuable intermediates.

In an other aspect, this invention relates to a process for the preparation of a compound of Formula I, as well as of its physiologically compatible salts,
(a) by reacting a compound of Formula III

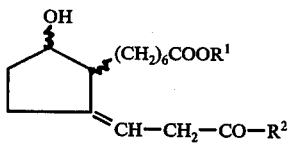

wherein $R^1$ and $R^2$ are as above, or one of its physiologically compatible salts, with a reducing agent or with a compound of Formula IV $$R^6 — M \qquad IV$$

wherein $R^6$ is alkyl of 1 to 5 carbon atoms, and M is MgCl, MgBr, MgI or lithium;
(b) by reacting a compound of Formula V

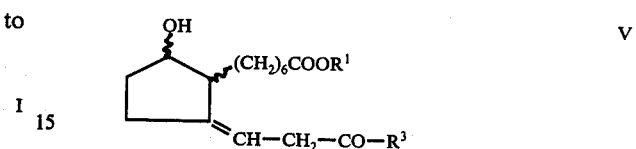

wherein $R^1$ and $R^3$ are as above or one of its physiologically compatible salts, with a compound of Formula VI $$R^2 — M \qquad VI$$

wherein $R^2$ and M are as above;
(c) by reacting a compound of Formula VII

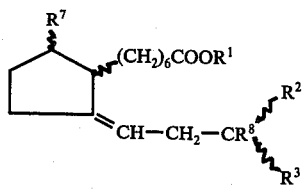

wherein one of the radicals $R^7$ or $R^8$ is functionally-modified OH and the other radical OH or functionally-modified OH, and $R^1$, $R^2$, and $R^3$ are as above, with a hydrolyzing agent;

(d) and/or converting a carboxylic acid of the Formula I ($R^1$ is H), by reaction with an esterifying agent, into an ester of Formula I ($R^1$ is alkyl of 1 – 4 carbon atoms), or converting an ester obtained of Formula I ($R^1$ is alkyl with 1 – 4 carbon atoms), by reaction with a solvolyzing agent, into an acid of Formula I, and/or separating a compound of Formula I into its racemates and/or enantiomers, and/or converting an acid of Formula I, by treatment with a base, into its physiologically compatible salts or liberating it from its salts by treatment with an an acid.

In another aspect, this invention relates to a process for the preparation of a compound of Formula II, wherein $R^1$, $R^2$, $R^4$ and A have the above-given meaning, by reacting a compound of Formula VIII

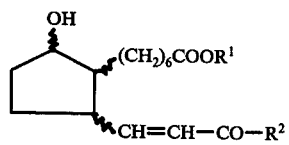

wherein $R^1$ and $R^2$ are as above with a ketalizing agent or a secondary amine $HNR^9R^{10}$ ($R^9$ and $R^{10}$ are as in Formula X) or with a compound of the Formula IX, $$R^5 — Y \qquad IX$$

wherein Y is Cl, Br, I or $—O—R^5$ and $R^5$ is as above, and the enamine possibly obtained of Formula X

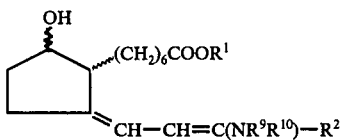

wherein R⁹ and R¹⁰ each are alkyl of 1 – 5 carbon atoms or cycloalkyl of up to 7 carbon atoms or collectively alkylene of up to 6 carbon atoms, possibly interrupted by —O—, —S—, or —NH—, reacted with a solvolyzing agent.

In another aspect this invention relates to pharmaceutical compositions containing at least one compound of the Formula I and/or one of its physiologically compatible salts, as well as a process for the preparation of pharmaceutical preparations, wherein at least one compound of Formula I is combined with solid, liquid or semi-liquid adjuvant or carrier materials and possibly together with a further active material into a suitable dosage form.

DETAILED DESCRIPTION

The compounds of Formula I contain 2 asymmetrical carbon-atoms in the five-membered ring. The carbon-atom in the 15-position substituted by the OH group is also asymmetrical, except when the two radicals $R^2$ and $R^3$ are the same. If $R^2$ and/or $R^3$ are branched alkyl further asymmetrical centers can also occur. In the formulae a wavy line (~) indicates a bond which can be in the α- or β-position.

In the above formulae, $R^1$ is hydrogen or an alkyl of 1 – 4 carbon atoms, such as methyl, ethyl, propyl, n-butyl, isopropyl, tert.-butyl or sec.-butyl. Hydrogen and unbranched alkyl are preferred.

$R^2$ is alkyl of 5 – 9 carbon atoms. Exemplary groups are pentyl, hexyl, heptyl, 3-methylbutyl, 2-methylbutyl, 1-methylbutyl, 2,2-dimethylpropyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 2-ethylbutyl, 1-ethylbutyl, 1,2,2-trimethylpropyl, 1,1,2-trimethylpropyl, 1-ethyl-2-methyl-propyl, 1-ethyl-1-methylpropyl, 5-methylhexyl, 4-methyl-hexyl, 3-methylhexyl, 2-methylhexyl, 1-methylhexyl, 4,4-dimethylpentyl, 3,3-dimethylpentyl, 2,2-dimethylpentyl, 1,1-dimethylpentyl, 1,2-dimethylpentyl, 3-ethylpentyl, 2-ethylpentyl, 1-ethylpentyl, 1,3,3-trimethylbutyl, 1,1,2,2-tetramethylpropyl, 6-methylheptyl, 5-methylheptyl, 4-methylheptyl, 3-methylheptyl, 2-methylheptyl, 1-methylheptyl, 5,5-dimethylhexyl, 1,1-dimethylhexyl, 1,2-dimethylhexyl, 7-methyloctyl, 2-methyloctyl, 1-methyloctyl, 6,6-dimethylheptyl, 1,1-dimethylheptyl or 1,2-dimethylheptyl. Pentyl, hexyl and heptyl are preferred.

$R^2$ is also phenoxymethyl or phenoxymethyl substituted by up to 3 of F, Cl, Br, CH₃, CF₃ or OCH₃, whereby the substituents are present on the phenyl ring. When the phenyl ring is trisubstituted, the substituents generally are different and not present in three adjacent positions. Exemplary substituents include 2,4-dichloro-, 3,4-dichloro-, 2,4-dibromo-, 2,4-dimethyl-, 3,4-dimethyl-, 2,4-dimethoxy-, 2,3-dimethoxy-, 3,4-dimethoxy, 2,4,6-trimethyl or 3,4,5-trimethoxyphenoxy-methyl radicals, but the unsubstituted phenoxymethyl and monosubstituted phenoxymethyl radicals are preferred, especially those substituted in the p-position. Thus, $R^2$ is preferably also p-fluoro-, p-chloro-, p-bromo-, p-methyl-, p-trifluoromethyl- or p-methoxyphenoxymethyl.

$R^3$ is hydrogen or alkyl of 1 – 5 carbon atoms, whether unbranched, such as methyl, ethyl, propyl, butyl or pentyl, or branched, such as isopropyl, isobutyl, sec.-butyl, tert.-butyl, 3-methylbutyl, 2-methylbutyl, 1-methylbutyl, 2,2-dimethylbutyl.

When $R^2$ in the compounds of Formula I is a branched alkyl radical, $R^3$ is because of possible steric hindrance, usually an unbranched alkyl radical, preferably methyl or ethyl, especially when the branching in $R^2$ is in the 1-position. If $R^2$ and $R^3$ are branched alkyl radicals, the branching in $R^3$ is as far removed as possible from the 1-position.

Especially preferred are compounds of Formula I in which at least one of $R^1$, $R^2$ and $R^3$ has one of the above preferred structures.

Preferred groups of compounds of this invention are those otherwise corresponding to Formula I but wherein:

Ia. $R^1$ is hydrogen;
Ib. $R^1$ is methyl or ethyl;
Ic. $R^2$ is pentyl;
Id. $R^2$ is 1-methylpentyl, including each of Ia – Ib;
Ie. $R^2$ is 1,1-dimethylpentyl, including each of Ia – Ib;
If. $R^2$ is phenoxymethyl, p-fluorophenoxymethyl, p-chlorophenoxymethyl, p-bromophenoxymethyl, p-methylphenoxymethyl, p-trifluoromethylphenoxymethyl or p-methoxyphenoxymethyl, including each of Ia – Ib;
Ig. $R^3$ is hydrogen, including each of Ia – If;
Ih. $R^3$ is methyl or ethyl, including each of Ia – If;
Ii. $R^1$ is hydrogen and $R^2$ pentyl;
Ij. $R^1$ is hydrogen and $R^3$ hydrogen or methyl;
Ik. $R^1$ is methyl or ethyl and $R^3$ hydrogen or methyl;
Il. $R^1$ is hydrogen or ethyl, $R^2$ pentyl, 1-methylpentyl or 1,1-dimethylpentyl and $R^3$ hydrogen or methyl, and
Im. $R^1$ is hydrogen or ethyl, $R^2$ phenoxymethyl, p-fluorophenoxymethyl, p-chlorophenoxymethyl, p-bromophenoxymethyl, p-methylphenoxymethyl, p-trifluoromethylphenoxymethyl or p-methoxyphenoxymethyl and $R^3$ hydrogen or methyl.

In Formula II, the radicals $R^1$, $R^2$, $R^4$ and A or $R^5$ and D have the values given above for Formula II.

$R^4$ is hydrogen or an acyl $R^5$.

$R^5$ is acyl of up to 4 carbon atoms, including alkanoyl, alkenoyl, alkynoyl and alkylsulfonyl, sulfo or phospho as well as alkanoyl substituted by one or more of fluorine, chlorine or bromine. Exemplary of $R^5$ are formyl, acetyl, propionyl, butyryl, isobutyryl, fluoroacetyl, chloroacetyl, bromoacetyl, dichloroacetyl, trifluoroacetyl, trichloroacetyl, acryloyl, propioloyl, methanesulfonyl, ethanesulfonyl or 2-hydroxyethanesulfonyl. Unsubstituted alkanoyl of up to 4 carbon atoms is preferred. As indicated above, $R^5$ can also be derived from an inorganic acid, such as, for example, sulfuric acid or phosphoric acid.

A is 2-oxoethylene-1,2 or the corresponding ketal or 2-acyloxyvinylene-1,2, wherein the acyloxy corresponds to $OR^5$ as above.

D is free or ketalized carbonyl group, which in ketalized form is dialkoxypolymethylene of up to 7 carbon atoms. Preferred ketals include dimethoxymethylene, diethoxymethylene or cyclic alkylenedioxymethylene of up to 4 carbon atoms, e.g., 1,3-dioxolan-2,2-diyl.

A is most preferably 2-oxoethylene-1,2, 2,2-dimethoxyethylene-1,2, 2,2-diethoxyethylene-1,2, 2,2-ethylenedioxyethylene-1,2 or 2-acetoxyvinylene-1,2.

Especially preferred intermediates are compounds of Formula II in which at least one of $R^1$, $R^2$, $R^4$, $R^5$, A and D is one of the above preferred groups.

These preferred groups of compounds are represented by the partial formulae IIa to IIf, which otherwise correspond to Formula II, and in which the symbols not more specifically defined are as in Formula II, wherein:

IIa. $R^1$ is hydrogen or ethyl;

IIb. $R^2$ is pentyl, 1-methylpentyl, 1,1-dimethylpentyl, phenoxymethyl, p-fluorophenoxymethyl, p-chlorophenoxymethyl, p-bromophenoxymethyl, p-methylphenoxymethyl, p-trifluoromethylphenoxymethyl or p-methoxyphenoxymethyl;

IIc. $R^4$ is hydrogen or acetyl;

IId. A is 2-oxoethylene-1,2, 2,2-ethylenedioxyethylene-1,2, or 2-acetoxyvinylene-1,2;

IIe. $R^1$ is hydrogen or ethyl, and $R^2$ is pentyl, 1-methylpentyl, 1,1-dimethylpentyl, phenoxymethyl, or p-fluorophenoxymethyl; and IIf. $R^1$ is hydrogen or ethyl, $R^2$ is pentyl, 1-methylpentyl, 1,1-dimethylpentyl, phenoxymethyl or p-fluorophenoxymethyl and A is 2-oxoethylene-1,2.

The compounds of Formula I, the preferred compounds of Formula I, especially those of the formulae Ia to Im, can occur in several stereoisomeric forms. As a rule, they occur as racemic mixtures. The same applies to the compounds of general Formula II, especially also to the preferred compounds of formulae IIa to IIf.

In the compounds of formulae III to X, the symbols $R^1$ to $R^{10}$, M and Y are as above.

$R^6$ is an alkyl radical of 1 – 5 carbon atoms and can, except for hydrogen, be the same as $R^3$.

The radicals $R^7$ and $R^8$ are a free or a functionally modified OH group, wherein at least one of the two radicals must be a functionally modified OH group.

Functionally modified hydroxyl groups include OH groups esterified with a saturated or unsaturated aliphatic, cycloaliphatic or aromatic, substituted or unsubstituted carboxylic or sulfonic acid or an inorganic acid. Preferred carboxylic acids are fatty acids of 1 – 18, most preferably 1 – 6 carbon atoms, e.g., formic, acetic, butyric, isobutyric, pivalic, trichloroacetic, benzoic, p-nitrobenzoic, palmitic, stearic or oleic acid.

Preferred sulfonic acids are those which are derived from alkylsulfonic acids of 1 – 6 carbon atoms, e.g., methane- or ethanesulfonic acid, or arylsulfonic acids of 6 – 10 carbon atoms, e.g., benzene-, p-toluene- or 1- and 2-naphthalenesulfonic acids. However, substituted sulfonic acids, such as 2-hydroxyethane- or 4-bromobenzenesulfonic acid, can also be used. Preferred inorganic acid esters are sulphates and phosphates.

Functionally modified OH can be an etherified OH group, e.g., aralkoxy of 7 – 19 carbon atoms, such as benzyloxy, p-methylbenzyloxy, 1- and 2-phenylethoxy, diphenylmethoxy, triphenylmethoxy or 1- or 2-naphthylmethoxy; alkoxy of up to 6 carbon atoms, preferably tert.-butoxy, tetrahydropyranyloxy, or trialkylsilyloxy, such as trimethylsilyloxy.

The radicals $R^9$ and $R^{10}$ each are alkyl of 1 – 6 carbon atoms, including methyl, ethyl, propyl, butyl, pentyl or hexyl; branched alkyl; cycloalkyl of up to 7 carbon atoms, such as cyclopentyl, cyclohexyl, cyclopropyl, cyclobutyl or cycloheptyl. The radicals $R^9$ and $R^{10}$ collectively are alkylene of up to 6 carbon atoms, preferably unbranched alkylene, including tetramethylene, pentamethylene or hexamethylene. If the alkylene group is interrupted by O, S or NH, then it preferably signifies $-CH_2CH_2-O-CH_2CH_2-$, $-CH_2CH_2-S-CH_2CH_2-$ or $-CH_2CH_2-NH-CH_2CH_2-$. $R^9$ and $R^{10}$ each are preferably branched or unbranched alkyl of 1 – 4 carbon atoms, cycloalkyl of 5 or 6 carbon atoms or collectively alkylene of 4 – 6 carbon atoms.

M is MgCl, MgBr, MgI or lithium.

Y is chlorine, bromine, iodine, or $OR^5$. $R^5$ preferably is as above, so that Y preferably is alkanoyloxy of up to 4 carbon atoms, e.g., acetoxy.

Compounds of the formulae I and II are derived from 7-(2-alkylcyclopentyl)-heptanoic acid. 7-(2-Octylcyclopentyl)heptanoic acid is named prostanoic acid when the two chains connected to the cyclopentane ring are in the trans-position. Compounds of Formulae I and II are, therefore, named as derivatives of 12-prostenoic acid.

Compounds of Formula I are 9,15-dihydroxy-12-prostenoic acids or their derivatives, preferably 9,15-dihydroxy-16-methyl-, 9,15-dihydroxy-16,16-dimethyl-, 9,15-dihydroxy-15-alkyl-, 9,15-dihydroxy-15-alkyl-16-methyl, 9,15-dihydroxy-15-alkyl-16,16-dimethyl, 9,15-dihydroxy-19,19-dimethyl-, 9,15-dihydroxy-15-alkyl-19,19,-dimethyl, 9,15-dihydroxy-20-homo-, 9,15-dihydroxy-16-methyl-20-homo-, 9,15-dihydroxy-16,16-dimethyl-20-homo-, 9,15-dihydroxy-15-alkyl-20-homo-, 9,15-dihydroxy-15-alkyl-16-methyl-20-homo-, 9,15-dihydroxy-15-alkyl-16,16,-dimethyl-20-homo-, 9,15-dihydroxy-20-bishomo-, 9,15-dihydroxy-16-methyl-20-bishomo-, 9,15-dihydroxy-16,16,-dimethyl-20-bishomo-, 9,15-dihydroxy-15-alkyl-20-bishomo-, 9,15-dihydroxy-15-alkyl-16-methyl-20-bishomo-, or 9,15-dihydroxy-15-alkyl-16,16-dimethyl-20-bishomo-12-prostenoic acid or the corresponding alkyl esters, especially ethyl esters. Especially preferred are the corresponding 15-methyl and 15-ethyl compounds or their alkyl esters, especially the ethyl esters.

Other compounds of Formula I include 16-phenyloxy derivatives of 9,15-dihydroxy-17,18,19,20-tetranor-12-prostenoic acid and its esters, preferably 9,15-dihydroxy-17,18,19,20-tetranor-16-phenoxy-, 9,15-dihydroxy-17,18,19,20-tetranor-16-p-fluorophenoxy-, 9,15-dihydroxy-17,18,19,20-tetranor-16-p-chlorophenoxy-, 9,15-dihydroxy-17,18,19,20-tetranor-16-p-bromophenoxy-, 9,15-dihydroxy-17,18,19,20-tetranor-16-p-methylphenoxy-, 9,15-dihydroxy-17,18,19,20-tetranor-16-p-trifluoromethylphenoxy, 9,15-dihydroxy-17,18,19,20-tetranor-16-p-methoxyphenoxy-, 9,15-dihydroxy-17,18,19,20-tetranor-15-alkyl-16-phenoxy-, 9,15-dihydroxy-17,18,19,20-tetranor-15-alkyl-16-p-fluorophenoxy, 9,15-dihydroxy-17,18,19,20-tetranor-15-alkyl-16-p-chlorophenoxy, 9,15-dihydroxy-17,18,19,20-tetranor-15-alkyl-16-p-bromophenoxy-, 9,15-dihydroxy-17,18,19,20-tetranor-15-alkyl-16-p-methylphenoxy-, 9,15-dihydroxy-17,18,19,20-tetranor-15-alkyl-16-p-trifluoromethoxy-, 9,15-dihydroxy-17,18,19,20-tetranor-15-alkyl-16-p-methoxyphenoxy-12-prostenoic acid or its alkyl esters, especially the ethyl esters. The 15-methyl and 15-ethyl derivatives are especially preferred.

Compounds of Formula II are 9-hydroxy-15-oxo-12-prostenoic acid or its derivatives, or derivatives of 9-hydroxy-15-oxo-17,18,19,20-tetranor-12-prostenoic acid. Preferred derivatives are 9-hydroxy-15-oxo-16-methyl-, 9-hydroxy-15-oxo-16,16-dimethyl-, 9-hydroxy-15-oxo-20-homo, 9-hydroxy-15-oxo-20-bishomo-, 9-hydroxy-15-oxo-16-methyl-20-homo-, 9-hydroxy-15-oxo-16,16-dimethyl-20-homo-, 9-hydroxy-15-oxo-16-methyl-20-bishomo-, 9-hydroxy-15-oxo-16,16-dimethyl- 20-bishomo-, 9-hydroxy-15-oxo-16,16-dimethyl-20-bishomo-, 9-hydroxy-15-oxo-17,18,19,20-tetranor-16-phenoxy-, 9-hydroxy-15-oxo-17,18,19,20-tetranor-16-p-fluorophenoxy-12-prostenoic acid or alkyl esters thereof, especially ethyl esters. Also preferred of compounds of Formula II are 9,15-diacyloxy-12,14-prostadienoic acids or their esters, especially the 9,15-diacetoxy derivatives.

Compounds of Formula III are derivatives of 9-hydroxy-15-oxo-12-prostenoic acid or of 9-hydroxy-15-oxo-17,18,19,20-tetranor-16-aryloxy-12-prostenoic acid or esters thereof. In these compounds, aryl is phenyl, or phenyl substituted by up to 3 of F, Cl, Br, $CH_3$, $CF_3$ or $OCH_3$.

Compounds of Formula IV are alkyl Grignard compounds of 1 – 5 carbon atoms or the corresponding alkyl lithium compounds. Exemplary compounds include methyl magnesium chloride, ethyl magnesium chloride, propyl magnesium chloride, butyl magnesium chloride, pentyl magnesium chloride, the corresponding magnesium bromides, magnesium iodides or lithium compounds, as well as branched alkyl magnesium halides or alkyl lithium compounds, including isopropyl magnesium chloride, isobutyl magnesium chloride or isopentyl magnesium chloride, the corresponding magnesium bromides, magnesium iodides or lithium compounds. Unbranched alkyl compounds are preferred.

The compounds of Formula V in which $R^3$ is H are 9-hydroxy-15-oxo-16,17,18,19,20-pentanor-12-prostenoic acid or esters thereof. When $R^3$ is alkyl of 1 – 4 carbon atoms in compounds of Formula V, the compounds are derivatives of 9-hydroxy-15-oxo-17,18,19,20-tetranor-12-prostenoic acid, -18,19,20-trisnor-12-prostenoic acid, -19,20-bisnor-12-prostenoic acid or -20-nor-12-prostenoic acids or esters thereof. When $R^3$ is alkyl of up to 5 carbon atoms, compounds of Formula V are preferably 9-hydroxy-15-oxo-12-prostenoic acid or an ester thereof.

Compounds of Formula VI are either alkyl Gignard reagents or alkyl lithium compounds of 5 – 9 carbon atoms or aryloxymethyl Grignard or lithium compounds. The unbranched compounds of 5 – 7 carbon atoms, such as pentyl magnesium chloride, hexyl magnesium chloride or heptyl magnesium chloride or the corresponding magnesium bromides, magnesium iodides or lithium compounds are preferred.

Aryloxymethyl Grignard or lithium compounds of Formula VI are phenoxymethyl magnesium bromide or phenoxymethyl magnesium bromide substituted by F, Cl, Br, $CH_3$, $CF_3$ or $CH_3O$. Monosubstituted, especially p-substituted compounds are preferred, e.g., p-fluorophenoxymethyl, p-chlorophenoxymethyl, p-bromophenoxymethyl, p-methylphenoxymethyl, p-trifluoromethylphenoxymethyl or p-methoxyphenoxymethyl magnesium bromide, the corresponding magnesium chlorides, magnesium iodides or lithium compounds.

Compounds of Formula VI can also be di- or tri-substituted phenoxymethyl Grignard compounds or lithium compounds, for example, 2,3-dichloro-, 2,5-dichloro-, 3,5-dichloro-, 2,5-dibromo-, 3,5-dibromo-, 2,3-dimethyl-, 2,5-dimethyl-, 2,6-dimethyl-, 3,5-dimethyl-, 2,6-dimethoxy-, 3,5-dimethoxy, 4-chloro-3-methoxy-, 2-chloro-5-methoxy-, 4-bromo-3-methoxy-, 2-bromo-5-methoxy-, 4-chloro-2-methyl-, 2-chloro-5-methyl-, 2-chloro-3,5-dimethoxy- or 4-chloro-3,5-dimethoxy-phenoxymethyl magnesium chloride, the corresponding magnesium bromides, magnesium iodides or lithium compounds.

Compounds of Formula VII are derivatives of 9,15-dihydroxy-12-prostenoic acid or of its esters in which at least one OH group is functionally modified. Preferred compounds are 9-monoacyl, 15-monoacyl or 9,15-diacyl derivatives of 12-prostenoic acid derivatives or of their esters named above as preferred compounds of Formula I, wherein the acyl radicals are selected preferably from those mentioned in connection with $R^7$ or $R^8$ above. The acyl radicals of $R^5$ are especially preferred.

Metal hydrides, especially complex metal hydrides are used as a reducing agent to convert a group wherein A is —CO— into a group wherein A is —CHOH—. Their reduction potential must not be so high that the $COOR^1$ group is reduced. Examples of suitable hydrides include sodium borohydride, possible in the presence of aluminum chloride or of lithium bromide; lithium borohydride and complex trialkyl borohydrides, such as lithium thexyllimonyl borane (J. Am. Chem. Soc. 93, 1491 [1971]); cyclic borohydrides, such as lithium perhydro-9b-boraphenalyl hydride (J. Am. Chem. Soc. 93, 7319 [1971]); calcium borohydride, magnesium borohydride; lithium and sodium alkoxy aluminum hydrides, e.g., LiAl (O-tert.—$C_4H_9$)$_3$H; sodium trialkoxy borohydrides, e.g., sodium trimethoxy borohydride. Aluminum alcoholates, e.g., triisopropyl or triisobutyl aluminum alcoholates, are also suitable in the presence of the alcoholate-forming alcohol, as reducing agent.

Hydrolytic reagents for reaction with compounds of Formula VII, as well as in other hydrolytic reactions, include water or water in admixture with organic solvents, in the presence of an acidic or basic catalyst. Organic solvents include alcohols of up to 7 carbon atoms, especially aliphatic alcohols, including methanol, ethanol, propanol, isopropyl alcohol, butanol, tert.-butyl alcohol, amyl alcohol, 2-methoxyethanol or 2-ethoxyethanol; ethers of up to 8 carbon atoms, preferably aliphatic or heterocyclic ethers, such as diethyl ether, diisopropyl ether, di-n-butyl ether, tetrahydrofuran (THF), dioxane, ethylene glycol dimethyl ether, ethylene glycol diethyl ether, or diethylene glycol dimethyl ether; acids, preferably aliphatic carboxylic acids of up to 4 carbon atoms, e.g., formic acid, acetic acid, propionic acid or butyric acid; esters of up to 8 carbon atoms, such as ethyl formate, ethyl acetate, ethyl butyrate, butyl acetate or butyl butyrate; ketones, preferably aliphatic ketones of up to 6 carbon atoms, such as acetone, butanone, pentan-3-one, 3-methylbutan-2-one or hexan-2-one; amines, preferably of up to 12 carbon atoms, most preferably aliphatic amines, such as triethylamine, ethanolamine, triethanolamine, diisopropylamine, di-n-butylamine or tri-n-butylamine, as well as alicyclic or heterocyclic amines, including cyclohexylamine, pyrrolidine, piperidine or pyridine; aprotic dipolar solvents, preferably amides, such as dimethylformamide (DMF) or hexamethyl phosphoric acid triamide (HMPT); nitriles, e.g., acetonitrile; or sulfur compounds, including dimethyl sulfoxide (DMSO) or tetrahydrothiophene-S,S-dioxide; and mixtures of these solvents, wherein at least one component of the mixtures is readily miscible with water.

Acidic catalysts for the hydrolysis include inorganic acids and organic acids. Examples of inorganic acids include hydrochloric, sulfuric, phosphoric or hydrobromic acids. Organic acids include carboxylic acids, such as chloroacetic acid, trichloroacetic acid or trifluoroacetic acid; sulfonic acids, such as methane-, ethane-, benzene- or p-toluenesulfonic acid.

Basic catalysts usable for hydrolysis include alkali metal or alkaline earth metal hydroxides, such as sodium, potassium or calcium hydroxide, or basic salts, such as sodium or potassium carbonate. Organic bases can also be employed as basic catalysts. Of these, amines, especially primary, secondary or tertiary amines, including aliphatic amines of up to 12 carbon atoms, for example, methyl-, dimethyl-, trimethyl-, ethyl-, diethyl-, triethyl-, isopropyl-, n-butyl- or tri-n-butylamine are preferred. Alicyclic amines, such as cyclohexylamine or dimethylaniline; heterocyclic amines, such as pyrrolidine, piperidine, morpholine, pyridine, α-picoline or quinoline; or quaternary ammonium hydroxides, e.g., tetramethyl ammonium hydroxide or benzyl trimethyl ammonium hydroxide can also be used. When the solvent is already basic or acidic, addition of a basic or of an acidic catalyst can be omitted.

Esterification reagents include, for example, alcohols of up to 4 carbon atoms, preferably in the presence of an inorganic or organic acid, such as HCl, HBr, HI, $H_2SO_4$, $H_3PO_4$, trifluoroacetic acid, a sulfonic acid, such as benzenesulfonic acid or p-toluene-sulfonic acid, or of an acidic ion exchanger; diazoalkanes, of up to 4 carbon atoms, preferably in the presence of acidic catalysts, e.g., $ZnCl_2$, $BF_3$, $H_2SO_4$, arylsulfonic acid, pyrophosphoric acid, boric acid, oxalic acid; alkyl halides of up to 4 carbon atoms, preferably bromides, such as ethyl, propyl, isopropyl or butyl bromide, or the corresponding chlorides or iodides; carboxylic acid or sulfonic acid alkyl esters, wherein the acidic residue is as desired and the alkyl radical contains up to 4 carbon atoms, preferably methyl, ethyl, propyl, isopropyl or butyl acetate, formate, methylsulfonate, ethylsulfonate or p-toluenesulfonate; and dialkyl sulfuric acid esters of up to 4 carbon atoms, such as dimethyl sulfate or diethyl sulfate.

Anhydrous organic solvents can be used as solvolyzing agents, as well as the above hydrolyzing agents. For a transesterification, alcohols of up to 4 carbon atoms, the aliphatic carboxylic acids of up to 4 carbon atoms, and esters of up to 8 carbon atoms are used. An acidic or basic catalyst is usually used. In addition to the catalysts suitable for hydrolysis, Lewis acids, such as $BF_3$, $BCl_3$, $AlCl_3$, $ZnCl_2$ or $SnCl_4$, are usable.

Compounds of Formula VIII are 9-hydroxy-15-oxo-13-prostenoic acid or of aryloxy-substituted derivatives of 9-hydroxy-15-oxo-17,18,19,20-tetranor-13-prostenoic acid, wherein $R^2$ is as above.

Compounds of Formula IX are acyl chlorides, bromides or iodides or acid anhydrides. Acyl radicals are those given for $R^5$. When a compound of Formula IX is an acid anhydride, a symmetrical anhydride is preferred. Especially preferred compounds of Formula IX are acetyl chloride, acetyl bromide, acetyl iodide and acetic anhydride.

Compounds of Formula X are derivatives of 9-hydroxy-15-amino-12,14-prostadienoic acid. Preferred compounds are the 15-dimethylamino, 15-diethylamino, 15-pyrrolidino, 15-piperidino, 15-morpholino and 15-thiomorpholino derivatives.

Ketalizing agents are alcohols, including monohydroxy aliphatic alcohols of up to 4 carbon atoms, unbranched, such as methanol, ethanol, propanol or butanol, or branched, such as isopropyl alcohol or isobutyl alcohol; dihydroxy aliphatic alcohols of 2 or 3 carbon atoms, such as ethylene glycol or 1,3-propylene glycol. The foregoing alcohols form ketals at carbonyl groups in the presence of an acidic catalyst. Acidic catalysts include those named above as hydrolyzing agents. Methanesulfonic acid, p-toluenesulfonic acid and sulfuric acid are preferred.

Chemical processes described below can be carried out under known reaction conditions. In particular, they can be carried out according to the processes described in the standard works of preparative organic chemistry, including HOUBEN-WEYL, Methoden der Organischen Chemic: Organic Reactions; and L. F. FIESER and M. FIESER, Reagents for Organic Synthesis, under reaction conditions known to be suitable for these reactions.

Compounds of Formula III, are obtained from the compounds of Formula VIII by reaction with a secondary amine. Preferred as secondary amines $HNR^9R^{10}$ are the ones mentioned above as basic catalysts for a hydrolysis. The reaction conditions are as given below.

In the reaction of a compound of Formula VIII with a secondary amine, an enamine of Formula X is formed as an intermediate. It is possible to isolate this enamine of Formula X and to prepare the corresponding compound of Formula III by reaction with a solvolyzing agent. Preferably, however, the secondary amine is allowed to react with a compound of Formula VIII and to prepare the compound of Formula III directly, without isolation of the enamine. In many cases, the enamine of Formula X formed as intermediate product was so sensitive than an enamine of Formula X could not be isolated.

Compounds of Formula IV are known or can be prepared by known methods, for example, by reaction of halides of the formula $R^6$—Cl, $R^6$—Br or $R^6$—I with magnesium, lithium or an alkyl lithium compound, such as n-butyl lithium, preferably in the presence of a suitable inert solvent.

The compounds of Formula V ($R^1 = CH_3$) can be obtained from known 7-(2-tetrahydropyranyloxy-5-formylcyclopentyl)-heptanoic acid methyl ester by reaction with a dimethyl-2-ketoalkyl phosphonate of the formula $(CH_3O)_2P(O)$—$CH_2COR^3$ in the presence of a strong base, hydrolytic cleavage of the tetrahydropyranyl protective group in the presence of an acidic catalyst and reaction of the 7-[2-hydroxy-5-(3-oxo-3-$R^3$-1-propenyl)-cyclopentyl]-heptanoic acid methyl ester obtained with a secondary amine. Other compounds of Formula V ($R^1$ is not $CH_3$) can also be prepared from the known 7-(2-tetrahydropyranyloxy-5-formyl-cyclopentyl)-heptanoic acid methyl ester after previous alkaline saponification and possible reesterification.

Compounds of Formula VI are known or can be prepared in known manner from known starting compounds, preferably from alkyl halides, or from phenoxymethyl halides possible substituted by up to three of F, Cl, Br, $CH_3$, $CF_3$ or $OCH_3$ and lithium or magnesium or an alkyl lithium compound, such as n-butyl lithium. The reactions can be carried out under the reaction conditions described in the literature for the preparation of such organometallic compounds.

Compounds of Formula VII ($R^1$ is $CH_3$, $R^7$ is tetrahydropyranyloxy, $R^8$ is OH), for example, can be prepared from known 7-(2-tetrahydropyranyloxy-5-formylcyclopentyl)-heptanoic acid methyl ester by reaction with a dimethyl 2-ketoalkyl phosphonate of the formula $(CH_3O)_2P(O)CH_2COR^3$ in the presence of a strong base, reaction of the 9-tetrahydropyranyloxy-15-oxo-13-prostenoic acid derivative obtained with a secondary amine, preferably without isolation of the intermediate enamine and reaction of the 9-tetrahydropyranyloxy-15-oxo-12-prostenioc acid derivative obtained with a compound of Formula VI. Other compounds of Formula VII ($R^1$ is not $CH_3$, $R^7$ is tetrahydropyranyloxy, $R^8$ is OH) can be prepared analogously from the corresponding starting compounds. The tetrahydropyranyloxy group of 7-(2-tetrahydropyranyloxy-5-formylcyclopentyl)-heptanoic acid methyl ester can also be interchanged in a known manner for another functionally reacted OH group and other compounds of Formula VII ($R^7$ is functionally modified OH other than tetrahydropyranyloxy) can be prepared by the reaction sequence given above.

Compounds of Formula VIII are known or can be prepared according to known processes from 7-(2-hydroxy-5-formylcyclopentyl)-heptanoic acid methyl ester, obtainable from the corresponding tetrahydropyranyloxy derivative by acidic saponification, by reaction with a dimethyl 2-ketoalkyl phosphonate or a substituted dimethyl-2-keto-3-phenoxypropyl phosphonate.

Compounds of Formula IX are known or can be prepared according to known processes.

Compounds of Formula II can be prepared from compounds of Formula VIII by reaction with a ketalizing agent. Generally, a suitable organic solvent and an acidic catalyst is used. Preferably, an excess of the ketalizing agent is used as solvent. The reaction temperatures are selected from between $-10°$ to the boiling point of the reaction mixture, preferably between $+10°$ and $+80°$. Reaction times depend on the reaction temperature and are, for example, between two hours and six hours.

Compounds of Formula II, especially $R^4$ and $R^5$ are the same, are obtained from compounds of Formula VIII by reaction with a compound of Formula IX. The reaction conditions for such acylation reactions are known. A suitable organic solvent and an acidic catalyst are usually employed. The solvent can be chosen from hydrocarbons, preferably of up to 8 carbon atoms, such as hexane, heptane, 2,2,4-trimethylpentane, cyclohexane, benzene or toluene; halogenated hydrocarbons, preferably an aliphatic halogenated hydrocarbon of up to 4 carbon atoms, such as methylene chloride, chloroform, carbon tetrachloride, dichloroethylene, perchlorobutandiene, or a halogenated aromatic hydrocarbon, such as chlorobenzene, ethers, such as diethyl ether, diisopropyl ether, tetrahydrofuran or dioxane; or mixtures of these solvents. It is especially advantageous to use an excess of the acylating agent as solvent, especially when it is a carboxylic acid anhydride. Temperatures between $-5°$ and the boiling point of the reaction mixture are preferred, most especially between room temperature and $+100°$ C. As a rule, the reaction times vary between one hour and 12 hours. The product of the reaction between a compound of general Formula VIII and a compound of general Formula IX is a compound of general Formula II in which A is —CH=•C(OR$^5$)—.

The reaction of a compound of general Formula VIII with a secondary amine $NHR^9R^{10}$ is carried out under reaction conditions usual for the formation of enamines, that is, using an organic solvent and an acidic or basic catalyst, preferably an alkali metal hydroxide or alkali metal carbonate. Suitable solvents include, besides the ones mentioned above for the reaction of a compound VIII with a compound of Formula IX, alcohols, especially aliphatic alcohols of up to 4 carbon atoms, such as methanol, ethanol, propanol, butanol, isopropyl alcohol or isobutyl alcohol; aprotic dipolar solvents, such as carboxylic acid amides, preferably dimethylformamide, dimethylacetamide, tetramethylurea or hexamethyl phosphoric acid triamide; carboxylic acid nitriles, such as acetonitrile; or organic sulfur compounds, such as dimethyl sulfoxide or tetrahydrothiophene-S,S-dioxide. The reaction temperatures vary between $+10°$ and the boiling temperature of the reaction mixture. The reaction times vary between 3 hours and 12 hours. It is especially advantageous to allow the reaction mixture to stand for a few hours, for example, 3 to 5 hours, at room temperature and subsequently to heat for a short time, for example, 0.5 to one hour, at temperatures between about 70° and 100°. As a rule, the compounds of Formula II are obtained directly. However, the intermediate enamines of Formula X can be isolated by distilling off most of the solvent; dissolving the residue in a low boiling, water immiscible solvent; extracting of the organic phase with water in order to remove the catalyst; drying the organic phase and distilling off the solvent. The enamines of Formula X thus obtained can easily be split to the compounds of Formula II by acidic catalysts in suitable inert organic solvents.

Reactions of compounds of Formula III or of physiologically compatible salts thereof with a reducing agent are carried out in an inert solvent, for example, an alcohol, such as methanol, ethanol or isopropyl alcohol; an ether, such as diethyl ether, tetrahydrofuran or dioxane; or in water or in mixtures of these solvents at temperatures between $-20°$ and 40°, preferably at room temperature. The reaction times vary between 15 minutes and 6 hours.

Reactions of compounds of Formula III with compounds of Formula IV, as well as of compounds of Formula V with compounds of Formula VI, are done in the solvents usual for such reactions, preferably in ethers, such as diethyl ether, diisopropyl ether, 1,2-dimethoxyethane, tetrahydrofuran, dioxane, anisole; benzene toluene, xylene or other hydrocarbons, or in mixtures of these solvents. The ketone of Formula III or of Formula V can be added to a solution of organometallic compound of Formula IV or VI or a solution of the organometallic compound can be added to a solution of the corresponding ketone. The reaction temperature is not critical and can be from approximately $-25°$ to room temperature. The adducts initially obtained from the reaction of a compound of Formula III with a compound of Formula IV or of a compound of Formula V with a compound of Formula VI are hydrolyzed in known manner, e.g., with water, aqueous salt solutions, such as ammonium chloride solutions, or aqueous acids, for example, aqueous acetic acid, to the compounds of Formula I. As a rule, the hydrolysis is done while the reaction mixture is being worked up.

The reaction of compounds of Formula VII with hydrolyzing agents is carried out at temperatures between $-20°$ and 100°. Usually, an acidic or a basic catalyst, preferably a basic catalyst, is used along with a suitable solvent.

Compounds of Formula I ($R^1$ is H) can be esterified according to known methods with an esterifying agent. A suitable inert, preferably anhydrous, solvent, for example, an ether, such as diethyl ether or tetrahydrofuran; an alcohol, preferably a lower branched or unbranched alkanol, such as methanol, ethanol, propanol, isopropyl alcohol or butanol; or hydrocarbon, such as petroleum ether, hexane, benzene or toluene; or mixtures of these solvents is used at temperatures between −10° and 40°, preferably at room temperature. The reaction times are, as a rule, between 30 minutes and 24 hours.

Esters of Formula I ($R^1$ is not H) can be converted into other compounds of Formula I (preferably $R^1$ is H) by treatment with solvolyzing agents. Basic hydrolysis to the acids of Formula I or their salts is preferred. Aqueous media, for example, mixtures of water with alcohols, preferably lower alkanols, such as methanol or ethanol, or with ethers, such as ethylene glycol monomethyl ether, ethylene glycol dimethyl ether, tetrahydrofuran or dioxane, at temperatures between 0° and 40°, preferably at room temperature, are preferred. The reactions times are approximately one hour to 12 hours.

Transesterifications are preferably carried out in anhydrous alcohols $R^1OH$, wherein $R^1$ is not H, the alkyl radical of which is to appear in the desired ester. Temperatures between 0° and 40°, preferably room temperature, are used.

Free carboxylic acids of Formula I ($R^1$ is H) can be converted by reaction with a base, into a physiologically acceptable metal or ammonium salt. These salts include sodium, potassium, magnesium, calcium and ammonium salts, as well as substituted ammonium salts, e.g., dimethyl and diethyl ammonium; monoethanol, diethanol and triethanol ammonium; cyclohexyl ammonium, dicyclohexyl ammonium and dibenzyl ethylene diammonium salts. On the other hand, acids of Formula I can be liberated from their metal and ammonium salts by treatment with acids, especially mineral acids, such as hydrochloric or sulfuric acid.

Compounds of Formula I have at least two and sometimes several asymmetrical centers. Therefore, they are usually obtained as mixtures of various stereoisomeric forms, i.e., as racemates or as mixtures of racemates. Since the various racemates are diastereomeric with respect to one another, they can be isolated from their mixtures and obtained in pure form on the basis of their differing physical properties. Techniques include recrystallization from suitable solvents, including the use of crystalline derivatives; distillative separation, chromatographic methods, including adsorption chromatography or partition chromatography and combinations thereof.

The racemates can be separated into their optical antipodes by a plurality of known methods. A method of chemical separation is preferred. In this method, diastereomers are formed by reaction between the racemic mixture and an optically-active adjuvant.

Thus, an optically-active base can be reacted with the carboxyl group of a compound of Formula I. For example, diastereomeric salts of the compounds of Formula I ($R^1$ is OH) can be formed with optically-active amines, such as quinine, cinchonidine, brucine, cinchonine, hydroxyhydrindamine, morphine, 1-phenylethylamine, 1-naphthylethylamine, phenyloxynaphthylmethylamine, quinidine, strychnine; basic amino acids, such as lysine, arginine, or amino acid esters. Similarly, ester diastereomers can be prepared by esterification of compounds of Formula I ($R^1$ is H) with optically-active alcohols, such as borneol, methol, or octan-2-ol. The difference in the solubility of the diastereomeric salts or esters obtained permits the selective crystallization of one form and the regeneration of the optically-active compounds in question from the mixture.

However, other functional groups present in the compounds of Formula I can also be employed for the formation of diastereomers. Thus, OH groups can be esterified with optically-active acids, such as (+)- and (−)-tartaric acid or campheric acid. Also, keto groups can be reacted with optically-active hydrazines, such as menthyl hydrazine. The pure enantiomers are obtained from these derivatives.

It is possible to obtain the optically-active compounds according to the described methods by using optically-active starting materials.

The compounds of Formula I are pharmacologically active. For example, they exhibit blood pressure-lowering activity, which can be shown, e.g., by continuous infusion of barbiturate-narcotized cats (40mg. sodium 5-(2-bromoalkyl)-5-sec.-butyl-barbiturate per kg.). The systemic blood pressure can be picked up by inserting a catheter into the femoral artery and connecting the catheter with a mercury manometer. The course of the blood pressure may be registered by means of a usual kymographion.

The prostenoic acid derivatives of Formula I also possess vasodilatory, anti-inflammatory, diuretic, bronchial-relaxing, gastric juice secretion-inhibiting thrombocyte aggregating, lipid decomposing and noradrenalin liberation-inhibiting, and nasal mucosal decongesting properties, as determined by methods conventional for this purpose. The prostenoic acid derivatives of Formula I can also influence the function of the corpus luteum, ova transport of ova through the Fallopian tubes, nidation of the uterus and male fertility. The inhibition of acid gastric secretion by the compounds of Formula I can be determined, by one method among others, in rats according to GOSH and SCHILD, Brit. J. Pharmacol., 13, 54 (1958). The bronchospasmolytic effect of the compounds of Formula I can be determined pharmacologically, e.g. in dogs, following the method of KONZETT and ROESSLER, Arch. exper. Path. u. Pharmakol., 195, 71 (1940).

Compounds of Formula I and/or their physiologically acceptable salts can be employed as pharmaceuticals and also as intermediate products for the preparation of other pharmaceuticals.

Due to their blood pressure lowering activity, the compounds of Formula I are useful as agents in human and veterinary medicine. They can be employed, for example, in the enteral or parenteral therapy of hypertension in substantially the same manner as the known compound prostaglandin $E_1$.

Because of their acid gastric secretion inhibiting activity the compounds of Formula I can be employed, for example in the enteral or parenteral therapy of ulcers too, in substantially the same manner as the known compound 15(R)15-methyl-prostaglandin $E_2$ methyl ester.

The new compounds can be used in human and veterinary medicine in admixture with solid, liquid and/or semi-liquid pharmaceutical carriers as pharmaceuticals. As carrier substances are used organic or inorganic materials which are suitable for parenteral, enteral or topical administration and which do not react with the new compounds, for example, water, vegetable oils, benzyl alcohols, polyethylene glycols, gelatine, lactose, starch, magnesium stearate, talc, vaseline and cholesterol. For parenteral administration solutions, preferably oily or aqueous solutions, as well as suspensions, emulsions or implants, are used. For enteral administration, tablets, dragees, syrups, juices or suppositories are suitable; for topical application salves, creams or powder. The above compositions can be sterilized or admixed with adjuvant materials, e.g., lubricants, preservatives, stabilizers, wetting agents, emulsifiers, salts for affecting osmotic pressure, buffers, coloring, flavoring and/or aroma materials.

The compounds of Formula I are generally administered to animals, including but not limited to mammals, e.g., household pets, humans, cattle, cats and dogs. The daily dosage of the active compounds in humans generally is about 0.05 to 5.0, preferably 0.1 to 2.5 mg./kg., usually in admixture with a pharmaceutically acceptable carrier. They are preferably administered in a dosage of 0.1 to 2.000 mg. per dosage unit. The dose can be administered singly or as divided dosages throughout the day.

The dosage is dependent upon the species treated, the form of administration and the purpose of treatment but it can be below or above the above-given values.

Parenteral administration is preferred, the compounds of this invention being particularly valuable in the treatment of hypertension. In this regard, they can be employed in substantially the same manner as the known compounds prostaglandin $E_1$ or prostaglandin $A_2$.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

The $R_f$ values were determined on thin layer finished plates of silica gel $F_{254}$ (E. Merck). If not otherwise indicated, the elution solution was a mixture of six parts by volume of dichloromethane and one part by volume of acetone. The IR spectra were recorded from films with a Perkin Elmer apparatus and reported as (IR) by giving the main bands.

UV spectra (UV) were recorded in a DK 2 A (Beckmann) apparatus in ethanol as solvent.

EXAMPLE 1

A mixture of 0.5 g 9β-hydroxy-15-oxo-13-prostenoic acid ethyl ester, 5 ml. acetic anhydride, 2 ml. acetyl chloride and 0.52 g. p-toluenesulfonic acid is heated for 3 hours, with the exclusion of moisture, at 100°; poured, after cooling, into 100 ml. ice water containing 15 g. NaHCO$_3$; and extracted twice with 50 ml. amounts of diethyl ether. The organic extract is washed until neutral with water, and dried over Na$_2$SO$_4$. After removal of the solvent and chromatographic purification (silica gel/petroleum ether/diisopropyl ether:triethylamine = 100:100:1), 9β,15-diacetoxy-12,14-prostadienoic acid ethyl ester is obtained. UV; 243–244 nm (ε = 19800).

By acetylation of the corresponding compounds of Formula VIII, the following are obtainable:
9β,15-diacetoxy-16-methyl-12,14-prostadienoic acid ethyl ester;
9β,15-diacetoxy-16,16-dimethyl-12,14-prostadienoic acid ethyl ester;
9β,15-diacetoxy-16-ethyl-12,14-prostadienoic acid ethyl ester;
9β,15-diacetoxy-19,19-dimethyl-12,14-prostadienoic acid ethyl ester;
9β,15-diacetoxy-20-homo-12,14-prostadienoic acid ethyl ester;
9β,15-diacetoxy-16-methyl-20-homo-12,14-prostadienoic acid ethyl ester;
9β,15-diacetoxy-16,16-dimethyl-20-homo-12,14-prostadienoic acid ethyl ester;
9β,15-diacetoxy-20-bishomo-12,14-prostadienoic acid ethyl ester;
9β,15-diacetoxy-16-methyl-20-bishomo-12,14-prostadienoic acid ethyl ester; and
9β,15-diacetoxy-16,16-dimethyl-20-bishomo-12,14-prostadienoic acid ethyl ester.

EXAMPLE 2

A mixture of 0.5 g. 9β-hydroxy-15-oxo-13-prostenoic acid ethyl ester, 7 ml. acetic anhydride and 0.5 ml. conc. H$_2$SO$_4$ is allowed to stand for 32 hours at room temperature, with the exclusion of moisture; poured into 100 ml. ice water; and extracted three times with 20 ml. amounts of methylene chloride. The organic phase is washed until neutral with water and dried over Na$_2$SO$_4$. After distillation of the solvent there is obtained, after chromatographic purification (silica gel/diisopropyl ether:petroleum ether:triethylamine - 100:100:1), 9β,15-diacetoxy-12,14-prostadienoic acid ethyl ester. UV: 243 – 244 nm (ε = 19800)

By acetylation of the corresponding compounds of Formula VIII, there are obtained:
9β,15-diacetoxy-17,18,19,20-tetranor-16-phenoxy-12,14-prostadienoic acid ethyl ester;
9β,15-diacetoxy-17,18,19,20-tetranor-16-p-fluorophenoxy-12,14-prostadienoic acid ethyl ester,
9β,15-diacetoxy-17,18,19,20-tetranor-16-p-chlorophenoxy-12,14-prostadienoic acid ethyl ester;
9β,15-diacetoxy-17,18,19,20-tetranor-16-p-bromophenoxy-12,14-prostadienoic acid ethyl ester;
9β,15-diacetoxy-17,18,19,20-tetranor-16-p-methylphenoxy-12,14-prostadienoic acid ethyl ester;
9β,15-diacetoxy-17,18,19,20-tetranor-16p-trifluoromethylphenoxy-12,14-prostadienoic acid ethyl ester, and
9β,15-diacetoxy-17,18,19,20-tetranor-16-p-methoxyphenoxy-12,14-prostadienoic acid ethyl ester.

EXAMPLE 3

A mixture of 0.5 g. 9β-hydroxy-15-oxo-13-prostenoic acid ethyl ester, 4 ml. acetyl bromide, 10 ml. benzene and 0.2 g. methanesulfonic acid is heated under reflux for four hours, with the exclusion of moisture and poured, after cooling, into 80 ml. ice water. The resulting mixture is extracted twice with 40 ml. amounts of benzene. The organic phase is washed with water until neutral and dried over Na$_2$SO$_4$. Solvent is removed and, after chromatographic purification (silica gel/diisopropyl ether:petroleum ether:triethylamine = 100:100:1), 9β,15-diacetoxy-12,14-prostadienoic acid ethyl ester is obtained. UV: 243 – 244 nm (ε = 19800)

EXAMPLE 4

A mixture of 1 g. 9β-hydroxy-15-oxo-13-prostenoic acid ethyl ester, 10 ml. acetic anhydride, 30 ml. glacial acetic acid and 1 g. benzenesulfonic acid is heated, with the exclusion of moisture, for 12 hours at 50°, poured onto 100 g. ice, and neutralized with solid NaHCO$_3$. The mixture is extracted twice with 30 ml. amounts of chloroform. The organic phase is washed to neutral with water and dried over Na$_2$SO$_4$. Solvent is removed and there is obtained, after chromatographic purification (silica gel/diisopropyl ether:petroleum ether:triethylamine = 100:100:1), 9β,15-diacetoxy-12,14-prostadienoic acid ethyl ester. UV: 243 – 244 nm ($\epsilon$ = 19800).

By acetylation of the corresponding compounds of Formula VIII, there are obtained:

9β,15-diacetoxy-12,14-prostadienoic acid methyl ester;
9β,15-diacetoxy-16-methyl-12,14-prostadienoic acid methyl ester;
9β,15-diacetoxy-16,16-dimethyl-12,14-prostadienoic acid methyl ester;
9β,15-diacetoxy-20-homo-12,14-prostadienoic acid methyl ester;
9β,15-diacetoxy-20-bishomo-12,14-prostadienoic acid methyl ester;
9β,15-diacetoxy-17,18,19,20-tetranor-16-p-fluorophenoxy-12,14-prostadienoic acid methyl ester;
9β,15-diacetoxy-12,14-prostadienoic acid propyl ester;
9β,15-diacetoxy-16-methyl-12,14-prostadienoic acid propyl ester;
9β,15-diacetoxy-16,16-dimethyl-12,14-prostadienoic acid propyl ester;
9β,15-diacetoxy-20-homo-12,14-prostadienoic acid propyl ester;
9β,15-diacetoxy-20-bishomo-12,14-prostadienoic acid propyl ester;
9β,15-diacetoxy-17,18,19,20-tetranor-16-p-fluorophenoxy-12,14-prostadienoic acid propyl ester;
9β,15-diacetoxy-12,14-prostadienoic acid butyl ester;
9β,15-diacetoxy-16-methyl-12,14-prostadienoic acid butyl ester;
9β,15-diacetoxy-16,16-dimethyl-12,14-prostadienoic acid butyl ester;
9β,15-diacetoxy-20-homo-12,14-prostadienoic acid butyl ester;
9β,15-diacetoxy-20-bishomo-12,14-prostadienoic acid butyl ester; and
9β,15-diacetoxy-17,18,19,20-tetranor-16-p-fluorophenoxy-12,14-prostadienoic acid butyl ester.

EXAMPLE 5

A mixture of 25 g. 9β-hydroxy-15-oxo-13-prostenoic acid ethyl ester, 6.3 ml. pyrrolidine, 312 mg. p-toluenesulfonic acid and 500 ml. dry benzene is stirred for 20 hours and heated under reflux in a nitrogen atmosphere, with moisture excluded, and water is removed. The mixture is diluted after cooling, with 600 ml. diethyl ether and washed with saturated aqueous NaCl solution until a pH value between 7 and 8 is reached. The organic phase is dried over $Na_2SO_4$. Solvent is removed and there is obtained, after chromatographic purification (silica gel/dichloromethane:petroleum ether:acetone = 5:5:1), 9β-hydroxy-15-oxo-12-prostenoic acid ethyl ester. IR: 3450, 1730, 1670 and 1630 $cm^{-1}$.

From the corresponding compounds of Formula VIII, by reaction with pyrrolidine in the presence of p-toluenesulfonic acid, there are obtained:

9β-hydroxy-15-oxo-16-methyl-12-prostenoic acid ethyl ester;
9β-hydroxy-15-oxo-16,16-dimethyl-12-prostenoic acid ethyl ester;
9β-hydroxy-15-oxo-20-homo-12-prostenoic acid ethyl ester;
9β-hydroxy-15-oxo-16-methyl-20-homo-12-prostenoic acid ethyl ester;
9β-hydroxy-15-oxo-16,16-dimethyl-20-homo-12-prostenoic acid ethyl ester;
9β-hydroxy-15-oxo-20-bishomo-12-prostenoic acid ethyl ester;
9β-hydroxy-15-oxo-16-methyl-20-bishomo-12-prostenoic acid ethyl ester; and
9β-hydroxy-15-oxo-16,16-dimethyl-20-bishomo-12-prostenoic acid ethyl ester.

EXAMPLE 6

A mixture of 12 g. 9β-hydroxy-15-oxo-13-prostenoic acid ethyl ester, 3 ml. piperidine, 1.2 g. methanesulfonic acid and 200 ml. dry chloroform is heated for 8 hours under nitrogen with exclusion of moisture. After cooling, the organic phase is washed with saturated NaCl solution until a pH value of about 7.5 is reached. The organic phase is dried over $Na_2SO_4$. Solvent is removed to obtain, after chromatographic purification (silica gel/dichloromethane:petroleum ether:acetone = 5:5:1), 9β-hydroxy-15-oxo-12-prostenoic acid ethyl ester. IR: 3450, 1730, 1670, and 1630 $cm^{-1}$.

From the corresponding compounds of Formula VIII, by reaction with piperidine in the presence of methanesulfonic acid, there are obtained:

9β-hydroxy-15-oxo-17,18,19,20-tetranor-16-phenoxy-12-prostenoic acid ethyl ester;
9β-hydroxy-15-oxo-17,18,19,20-tetranor-16-p-fluorophenoxy-12-prostenoic acid ethyl ester;
9β-hydroxy-15-oxo-17,18,19,20-tetranor-16-p-chlorophenoxy-12-prostenoic acid ethyl ester;
9β-hydroxy-15-oxo-17,18,19,20-tetranor-16-p-bromophenoxy-12-prostenoic acid ethyl ester;
9β-hydroxy-15-oxo-17,18,19,20-tetranor-16-p-methylphenoxy-12-prostenoic acid ethyl ester;
9β-hydroxy-15-oxo-17,18,19,20-tetranor-16-p-trifluoromethylphenoxy-12-prostenoic acid ethyl ester; and
9β-hydroxy-15-oxo-17,18,19,20-tetranor-16-p-methoxyphenoxy-12-prostenoic acid ethyl ester.

EXAMPLE 7

A mixture of 4 g. 9β-hydroxy-15-oxo-13-prostenoic acid ethyl ester, 1 ml. morpholine, 012 g. potassium carbonate, 5 ml. dry DMF and 50 ml. dry benzene is allowed to stand for 24 hours at room temperature under nitrogen and with the exclusion of moisture, then heated under reflux for 45 minutes. The solution is washed until neutral with saturated NaCl solution. The organic phase is dried over $Na_2SO_4$ and solvent is removed to obtain, after chromatographic purification (silica gel/dichloromethane:petroleum ether:acetone = 5:5:1), 9β-hydroxy-15-oxo-12-prostenoic acid ethyl ester. IR: 3450, 1730, 1670 and 1630 $cm^{-1}$.

From the corresponding compounds of Formula VIII by reaction with morpholine in the presence of potassium carbonate, there are obtained:

9β-hydroxy-15-oxo-12-prostenoic acid methyl ester;
9β-hydroxy-15-oxo-16-methyl-12-prostenoic acid methyl ester;
9β-hydroxy-15-oxo-16,16-dimethyl-12-prostenoic acid methyl ester;
9β-hydroxy-15-oxo-20-homo-12-prostenoic acid methyl ester;
9β-hydroxy-15-oxo-20-bishomo-12-prostenoic acid methyl ester;
9β-hydroxy-15-oxo-17,18,19,20-tetranor-16-p-fluorophenoxy-12-prostenoic acid methyl ester;
9β-hydroxy-15-oxo-12-prostenoic acid propyl ester;
9β-hydroxy-15-oxo-16-methyl-12-prostenoic acid propyl ester;

9β-hydroxy-15-oxo-16,16-dimethyl-12-prostenoic acid propyl ester;

9β-hydroxy-15-oxo-20-homo-12-prostenoic acid propyl ester;

9β-hydroxy-15-oxo-20-bishomo-12-prostenoic acid methyl ester;

9β-hydroxy-15-oxo-17,18,19,20-tetranor-16-p-fluorophenoxy-12-prostenoic acid propyl ester;

9β-hydroxy-15-oxo-12-prostenoic acid butyl ester;

9β-hydroxy-15-oxo-16-methyl-12-prostenoic acid butyl ester;

9β-hydroxy-15-oxo-16,16-dimethyl-12-prostenoic acid butyl ester;

9β-hydroxy-15-oxo-20-homo-12-prostenoic acid butyl ester;

9β-hydroxy-15-oxo-20-bishomo-12-prostenoic acid butyl ester; and

9β-hydroxy-15-oxo-17,18,19,20-tetranor-16-p-fluorophenoxy-12-prostenoic acid butyl ester.

EXAMPLE 8

9α-Hydroxy-15-oxo-13-prostenoic acid ethyl ester is converted by the procedure of Example 5, by reaction with pyrrolidine in the presence of p-toluenesulfonic acid to 9α-hydroxy-15-oxo-12-prostenoic acid ethyl ester. IR: 3500, 1720, 1620 cm$^{-1}$.

From the corresponding compounds of Formula VIII, by reaction with pyrrolidine in the presence of p-toluenesulfonic acid, there are obtained:

9α-hydroxy-15-oxo-16-methyl-12-prostenoic acid ethyl ester;

9α-hydroxy-15-oxo-16,16-dimethyl-12-prostenoic acid ethyl ester;

9α-hydroxy-15-oxo-20-homo-12-prostenoic acid ethyl ester;

9α-hydroxy-15-oxo-16-methyl-20-homo-12-prostenoic acid ethyl ester;

9α-hydroxy-15-oxo-16,16-dimethyl-20-homo-12-prostenoic acid ethyl ester;

9α-hydroxy-15-oxo-20-bishomo-12-prostenoic acid ethyl ester;

9α-hydroxy-15-oxo-16-methyl-20-bishomo-12-prostenoic acid ethyl ester; and

9α-hydroxy-15-oxo-16,16-dimethyl-20-bishomo-12-prostenoic acid ethyl ester.

EXAMPLE 9

9α-Hydroxy-15-oxo-13-prostenoic acid ethyl ester is converted, by the procedure of Example 6, by reaction with piperidine in the presence of methanesulfonic acid, to 9α-hydroxy-15-oxo-12-prostenoic acid ethyl ester. IR: 3500, 1720, 1620 cm$^{-1}$.

From the corresponding compounds of Formula VIII, by reaction with piperidine in the presence of methanesulfonic acid, there are obtained:

9α-hydroxy-15-oxo-17,18,19,20-tetranor-16-phenoxy-12-prostenoic acid ethyl ester;

9α-hydroxy-15-oxo-17,18,19,20-tetranor-16-p-fluorophenoxy-12-prostenoic acid ethyl ester;

9α-hydroxy-15-oxo-17,18,19,20-tetranor-16-p-chlorophenoxy-12-prostenoic acid ethyl ester;

9α-hydroxy-15-oxo-17,18,19,20-tetranor-16-p-bromophenoxy-12-prostenoic acid ethyl ester;

9α-hydroxy-15-oxo-17,18,19,20-tetranor-16-p-methylphenoxy-12-prostenoic acid ethyl ester;

9α-hydroxy-15-oxo-17,18,19,20-tetranor-16-p-trifluoromethylphenoxy-12-prostenoic acid ethyl ester; and 9α-hydroxy-15-oxo-17,18,19,20-tetranor-16-p-methoxyphenoxy-12-prostenoic acid ethyl ester.

EXAMPLE 10

9α-Hydroxy-15-oxo-13-prostenoic acid ethyl ester is converted, by the procedure of Example 7, by reaction with morpholine in the presence of potassium carbonate, to 9α-hydroxy-15-oxo-12-prostenoic acid ethyl ester. IR: 3500, 1720, 1620 cm$^{-1}$.

From the corresponding compounds of Formula VIII, by reaction with morpholine in the presence of potassium carbonate, there are obtainable:

9α-hydroxy-15-oxo-12-prostenoic acid methyl ester;

9α-hydroxy-15-oxo-15-methyl-12-prostenoic acid methyl ester;

9α-hydroxy-15-oxo-16,16-dimethyl-12-prostenoic acid methyl ester;

9α-hydroxy-15-oxo-20-homo-12-prostenoic acid methyl ester;

9α-hydroxy-12-oxo-20-bishomo-12-prostenoic acid methyl ester;

9α-hydroxy-15-oxo-17,18,19,20-tetranor-16-p-fluorophenoxy-12-prostenoic acid methyl ester;

9α-hydroxy-15-oxo-12-prostenoic acid propyl ester;

9α-hydroxy-15-oxo-16-methyl-12-prostenoic acid propyl ester;

9α-hydroxy-15-oxo-16,16-dimethyl-12-prostenoic acid propyl ester;

9α-hydroxy-15-oxo-20-homo-12-prostenoic acid propyl ester;

9α-hydroxy-15-oxo-20-bishomo-12-prostenoic acid propyl ester;

9α-hydroxy-15-oxo-20-bishomo-12-prostenoic acid propyl ester;

9α-hydroxy-15-oxo-17,18,19,20-tetranor-16-p-fluorophenoxy-12-prostenoic acid propyl ester;

9α-hydroxy-15-oxo-12-prostenoic acid butyl ester;

9α-hydroxy-15-oxo-16-methyl-12-prostenoic acid butyl ester;

9α-hydroxy-15-oxo-16,16-dimethyl-12-prostenoic acid butyl ester;

9α-hydroxy-15-oxo-20-homo-12-prostenoic acid butyl ester;

9α-hydroxy-15-oxo-20-bishomo-12-prostenoic acid butyl ester; and

9α-hydroxy-15-oxo-17,18,19,20-tetranor-16-p-fluorophenoxy-12-prostenoic acid butyl ester.

EXAMPLE 11

A mixture of 257 mg. 9β-acetoxy-15-hydroxy-12-prostenoic acid ethyl ester, 4 ml. dioxane and 2 ml. 1N aqueous KOH for 20 hours is stirred at room temperature under nitrogen and then acidified with 5% sulfuric acid (pH about 2) and extracted three times with 6 ml. amounts of diethyl ether. The organic phase is washed to neutral with water and dried over Na$_2$SO$_4$. The solvent is removed and there is obtained, after chromatographic purification of the residue (silica gel/ethyl acetate:cyclohexane:acetic acid = 50:50:1), 9β,15-dihydroxy-12-prostenoic acid. R$_f$ = 0.08, IR: 3370, 1710, 1570 cm$^{-1}$.

The starting material is prepared by adding to 1.3 g. 9β,15-dihydroxy-12,14-prostadienoic acid ethyl ester, dissolved in 15 ml. dry ethanol, with stirring and exclusion of moisture, at room temperature, at intervals of 30 minutes, five 120 mg. portions of NaBH$_4$. The mixture is acidified with glacial acetic acid and poured into 80 ml. water with cooling. The solution is extracted with dichloromethane and the organic phase washed to neutral with water, and dried over MgSO$_4$. Solvent is removed to yield, after chromatographic purification (silica gel/-diisopropyl ether), 9β-acetoxy-15-hydroxy-12-prostenoic acid ethyl ester. R$_f$ = 0.56. IR: 3500, 1720, and 1450 cm$^{-1}$.

EXAMPLE 12

Compounds of Formula VII (preparable from the corresponding compounds of Formula II by reduction with NaBH$_4$), are converted by hydrolysis, following the procedure of Example 11, to:
9β,15-dihydroxy-16-methyl-12-prostenoic acid;
9β,15-dihydroxy-16,16-dimethyl-12-prostenoic acid;
9β,15-dihydroxy-16-ethyl-12-prostenoic acid;
9β,15-dihydroxy-19,19-dimethyl-12-prostenoic acid;
9β,15-dihydroxy-20-homo-12-prostenoic acid;
9β,15-dihydroxy-16-methyl-20-homo-12-prostenoic acid;
9β,15-dihydroxy-16,16-dimethyl-20-homo-12-prostenoic acid;
9β,15-dihydroxy-20-bishomo-12-prostenoic acid;
9β,15-dihydroxy-16-methyl-20-bishomo-12-prostenoic acid;
9β,15-dihydroxy-16,16-dimethyl-20-bishomo-12-prostenoic acid;
9β,15-dihydroxy-17,18,19,20-tetranor-16-phenoxy-12-prostenoic acid;
9β,15-dihydroxy-17,18,19,20-tetranor-16-p-fluorophenoxy-12-prostenoic acid;
9β,15-dihydroxy-17,18,19,20-tetranor-16-p-chlorophenoxy-12-prostenoic acid;
9β,15-dihydroxy-17,18,19,20-tetranor-16-p-bromophenoxy-12-prostenoic acid;
9β,15-dihydroxy-17,18,19,20-tetranor-16-p-methylphenoxy-12-prostenoic acid;
9β,15-dihydroxy-17,18,19,20-tetranor-16-p-trifluoromethyl-phenoxy-12-prostenoic acid; and
9β,15-dihydroxy-17,18,19,20-tetranor-16-p-methoxyphenoxy-12-prostenoic acid.

EXAMPLE 13

(a) A mixture of 160 mg. 9β-acetoxy-15-hydroxy-12-prostenoic acid ethyl ester, 8 ml. dioxane, 3 ml. DMF and 1 ml. 1N aqueous NaOH is stirred for 8 hours at 45° under argon, acidified with 1N aqueous sulfuric acid (pH value about 3), extracted 2 times with 10 ml. amounts of chloroform and the extracts dried over Na$_2$SO$_4$. Solvent is removed to obtain, after chromatographic purification of the residue (silica gel/ethyl acetate:cyclohexane:acetic acid = 50:50:1), 9β,15-dihydroxy-12-prostenoic acid. R$_f$ = 0.08. IR: 3370, 1710, 1570 cm$^{-1}$.

(b) 340 mg. 9β,15-dihydroxy-12-prostenoic acid, dissolved in 15 ml. dry diethyl ether, is added dropwise to 10 ml. of a solution of sodium ethylate in dry ehtanol, prepared by dissolving of 240 mg. sodium in 100 ml. dry ehtanol. After 15 minutes, the solvent is removed. The residue is the sodium salt of 9β,15-dihydroxy-12-prostenoic acid.

(c) To 73 mg. of the sodium salt of 9β,15-dihydroxy-12-prostenoic acid, dissolved in a mixture of 10 ml. water and 4 ml. dioxane and 3 ml. 0.1 normal aqueous HCl, is added 10 ml. saturated aqueous NaCl solution. The mixture is extracted three times with 10 ml. amounts of diethyl ether. The organic phase is washed twice with 15 ml. amounts of water and dried over MgSO$_4$. The solvent is removed and 9β,15-dihydroxy-12-prostenoic acid, is obtained as residue. R$_f$ = 0.08.

EXAMPLE 14

To 2 g. 9β-hydroxy-15-oxo-12-prostenoic acid ethyl ester, dissolved in 20 ml. dry ethanol, is added with ice cooling under nitrogen with exclusion of moisture and stirring, portionwise over 15 minutes, 206 mg. NaBH$_4$. The mixture is stirred 15 minutes more and 0.325 ml. glacial acetic acid is added dropwise thereto. The mixture is poured into 50 ml. of water. Solvent is removed by distillation and the residue is extracted three times with 15 ml. amounts of diethyl ether. The organic phase is washed with water and dried over Na$_2$SO$_4$. Solvent is removed to obtain as residue 9β,15-dihydroxy-12-prostenoic acid ethyl ester which, after chromatographic purification twice (first silica gel/dichloromethane:acetone = 10:1; then silica gel/petroleum ether:ethanol = 9:1), can be separated into the two 15-epimers:
epimer A: R$_f$ = 0.27
epimer B: R$_f$ = 0.22.

From the corresponding compounds of Formula III, by reduction with NaBH$_4$, are obtained analogously:
9β,15-dihydroxy-16-methyl-12-prostenoic acid ethyl ester;
9β,15-dihydroxy-16,16-dimethyl-12-prostenoic acid ethyl ester;
9β,15-dihydroxy-16-ethyl-12-prostenoic acid ethyl ester;
9β,15-dihydroxy-19,19-dimethyl-12-prostenoic acid ethyl ester;
9β,15-dihydroxy-20-homo-12-prostenoic acid ethyl ester;
9β,15-dihydroxy-16-methyl-20-homo-12-prostenoic acid ethyl ester;
9β,15-dihydroxy-16,16-dimethyl-20-homo-12-prostenoic acid ethyl ester;
9β,15-dihydroxy-20-bishomo-12-prostenoic acid ethyl ester;
9β,15-dihydroxy-16-methyl-20-bishomo-12-prostenoic acid ethyl ester;
9β,15-dihydroxy-16,16-dimethyl-20-bishomo-12-prostenoic acid ethyl ester;
9β,15-dihydroxy-17,18,19,20-tetranor-16-phenoxy-12-p-prostenoic acid ethyl ester;
9β,15-dihydroxy-17,18,19,20-tetranor-16-p-fluorophenoxy-12-prostenoic acid ethyl ester;
9β,15-dihydroxy-17,18,19,20-tetranor-16-p-chlorophenoxy-12-prostenoic acid ethyl ester;
9β,15-dihydroxy-17,18,19,20-tetranor-16-p-bromophenoxy-12-prostenoic acid ethyl ester;
9β,15-dihydroxy-17,18,19,20-tetranor-16-p-methylphenoxy-12-prostenoic acid ethyl ester;
9β,15-dihydroxy-17,18,19,20-tetranor-16-p-trifluoromethyl-phenoxy-12-prostenoic acid ethyl ester;
9β,15-dihydroxy-17,18,19,20-tetranor-16-p-methoxyphenoxy-12-prostenoic acid ethyl ester;
9β,15-dihydroxy-12-prostenoic acid methyl ester;
9β,15-dihydroxy-16-methyl-12-prostenoic acid methyl ester;
9β,15-dihydroxy-16,16-dimethyl-12-prostenoic acid methyl ester;
9β,15-dihydroxy-20-homo-12-prostenoic acid methyl ester;
9β,15-dihydroxy-20-bishomo-12-prostenoic acid methyl ester;

9β,15-dihydroxy-17,18,19,20-tetranor-16-p-fluorophenoxy-12-prostenoic acid methyl ester;
9β,15-dihydroxy-12-prostenoic acid propyl ester;
9β,15-dihydroxy-16-methyl-12-prostenoic acid propyl ester;
9β,15-dihydroxy-16,16-dimethyl-12-prostenoic acid propyl ester;
9β,15-dihydroxy-20-homo-12-prostenoic acid propyl ester;
9β,15-dihydroxy-20-bishomo-12-prostenoic acid propyl ester;
9β,15-dihydroxy-17,18,19,20-tetranor-16-p-fluorophenoxy-12-prostenoic acid propyl ester;
9β,15-dihydroxy-12-prostenoic acid butyl ester;
9β,15-dihydroxy-16-methyl-12-prostenoic acid butyl ester;
9β,15-dihydroxy-16,16-dimethyl-12-prostenoic acid butyl ester;
9β,15-dihydroxy-20-homo-12-prostenoic acid butyl ester;
9β,15-dihydroxy-20-bishomo-12-prostenoic acid butyl ester; and
9β,15-dihydroxy-17,18,19,20-tetranor-16-p-fluorophenoxy-12-prostenoic acid butyl ester.

EXAMPLE 15

9α-Hydroxy-15-oxo-12-prostenoic acid ethyl ester is converted by reduction with NaBH$_4$, following the procedure of Example 14, to the two 15-epimers of 9α,15-dihydroxy-12-prostenoic acid ethyl ester;
epimer A: $R_f = 0.29$
epimer B: $R_f = 0.25$.

The corresponding compounds of Formula III are converted by reduction with NaBH$_4$ to:
9α,15-dihydroxy-16-methyl-12-prostenoic acid ethyl este;
9α,15-dihydroxy-16,16-dimethyl-12-prostenoic acid ethyl ester;
9α,15-dihydroxy-16-ethyl-12-prostenoic acid ethyl ester;
9α,15-dihydroxy-19,19-dimethyl-12-prostenoic acid ethyl ester;
9α,15-dihydroxy-20-homo-12-prostenoic acid ethyl ester;
9α,15-dihydroxy-16-methyl-20-homo-12-prostenoic acid ethyl ester;
9α,15-dihydroxy-16,16-dimethyl-20-homo-12-prostenoic acid ethyl ester;
9α,15-dihydroxy-20-bishomo-12-prostenoic acid ethyl ester;
9α,15-dihydroxy-16-methyl-20-bishomo-12-prostenoic acid ethyl ester;
9α,15-dihydroxy-16,16-dimethyl-20-bishomo-12-prostenoic acid ethyl ester;
9α,15-dihydroxy-17,18,19,20-tetranor-16-phenoxy-12-prostenoic acid ethyl ester;
9α,15-dihydroxy-17,18,19,20-tetranor-16-p-fluorophenoxy-12-prostenoic acid ethyl ester;
9α,15-dihydroxy-17,18,19,20-tetranor-16-p-chlorophenoxy-12-prostenoic acid ethyl ester;
9α,15-dihydroxy-17,18,19,20-tetranor-16-p-bromophenoxy-12-prostenoic acid ethyl ester;
9α,15-dihydroxy-17,18,19,20-tetranor-16-p-methylphenyl-12-prostenoic acid ethyl ester;
9α,15-dihydroxy-17,18,19,20-tetranor-16-p-trifluoromethyl-phenoxy-12-prostenoic acid ethyl ester;
9α,15-dihydroxy-17,18,19,20-tetranor-16-p-methoxyphenoxy-12-prostenoic acid ethyl ester;
9α,15-dihydroxy-12-prostenoic acid methyl ester;
9α,15-dihydroxy-16-methyl-12-prostenoic acid methyl ester;
9α,15-dihydroxy-16,16-dimethyl-12-prostenoic acid methyl ester;
9α,15-dihydroxy-20-homo-12-prostenoic acid methyl ester;
9α,15-dihydroxy-20-bishomo-12-prostenoic acid methyl ester;
9α,15-dihydroxy-17,18,19,20-tetranor-16-p-fluorophenoxy-12-prostenoic acid methyl ester;
9α,15-dihydroxy-12-prostenoic acid propyl ester;
9α,15-dihydroxy-16-methyl-12-prostenoic acid propyl ester;
9α,15-dihydroxy-16,16-dimethyl-12-prostenoic acid propyl ester;
9α,15-dihydroxy-20-homo-12-prostenoic acid propyl ester;
9α,15-dihydroxy-20-bishomo-12-prostenoic acid propyl ester;
9α,15-dihydroxy-17,18,19,20-tetranor-16-p-fluorophenoxy-12-prostenoic acid propyl ester;
9α,15-dihydroxy-12-prostenoic acid butyl ester;
9α,15-dihydroxy-16-methyl-12-prostenoic acid butyl ester;
9α,15-dihydroxy-16,16-dimethyl-12-prostenoic acid butyl ester;
9α,15-dihydroxy-20-homo-12-prostenoic acid butyl ester;
9α,15-dihydroxy-20-bishomo-12-prostenoic acid butyl ester; and
9α,15-dihydroxy-17,18,19,20-tetranor-16-p-fluorophenoxy-12-prostenoic acid butyl ester.

EXAMPLE 16

Methyl magnesium iodide (prepared from 816 mg. magnesium filings and 2.12 ml. methyl iodide) dissolved in 80 ml. dry diethyl ether is added dropwise to 3.9 g. 9β-hydroxy-15-oxo-12-prostenoic acid ethyl ester, dissolved in 200 ml. dry diethyl ether, with the exclusion of moisture, under nitrogen and with stirring. The mixture is stirred for 15 minutes more at room temperature and mixed dropwise, with ice cooling, with 300 ml. saturated aqueous NH$_4$Cl solution. The organic phase is separated, washed with water and dried over Na$_2$SO$_4$. The solvent is removed by distillation to yield as residue 9β,15-dihydroxy-15-methyl-12-prostenoic acid ethyl ester, which is separated chromatographically (first silica gel/dichloromethane:acetone = 10:1; then silica gel/petroleum ether:ethanol = 9:1) into the two 15-epimers;
epimer A: $R_f = 0.20$
epimer B: $R_f = 0.27$.

The corresponding compounds of Formula III are treated with methyl magnesium iodide to obtain:
9β,15-dihydroxy-15,16-dimethyl-12-prostenoic acid ethyl ester;
9β,15-dihydroxy-15,16,16-trimethyl-12-prostenoic acid ethyl ester;
9β,15-dihydroxy-15-methyl-20-homo-12-prostenoic acid ethyl ester;
9β,15-dihydroxy-15,16-dimethyl-20-homo-12-prostenoic acid ethyl ester;
9β,15-dihydroxy-15,16,16-trimethyl-20-homo-12-prostenoic acid ethyl ester;

9β,15-dihydroxy-15-methyl-20-bishomo-12-prostenoic acid ethyl ester;

9β,15-dihydroxy-15,16-dimethyl-20-bishomo-12-prostenoic acid ethyl ester;

9β,15-dihydroxy-15,16,16-trimethyl-20-bishomo-12-prostenoic acid ethyl ester;

9β,15-dihydroxy-17,18,19,20-tetranor-15-methyl-16-phenoxy-12-prostenoic acid ethyl ester;

9β,15-dihydroxy-17,18,19,20-tetranor-15-methyl-16-p-fluorophenoxy-12-prostenoic acid ethyl ester;

9β,15-dihydroxy-17,18,19,20-tetranor-15-methyl-16-p-chlorophenoxy-12-prostenoic acid ethyl ester;

9β,15-dihydroxy-17,18,19,20-tetranor-15-methyl-16-p-bromophenoxy-12-prostenoic acid ethyl ester;

9β,15-dihydroxy-17,18,19,20-tetranor-15-methyl-16-p-methylphenoxy-12-prostenoic acid ethyl ester;

9β,15-dihydroxy-17,18,19,20-tetranor-15-methyl-16-p-trifluoromethylphenoxy-12-prostenoic acid ethyl ester; and 9β,15-dihydroxy-17,18,19,20-tetranor-12-methyl-16-p-methoxyphenoxy-12-prostenoic acid ethyl ester.

EXAMPLE 17

Ethyl magnesium iodide (prepared from 720 mg. magnesium filings and 4.7 g. ethyl iodide) dissolved in 75 ml. dry diethyl ether is added dropwise to 3.7 g. 9β-hydroxy-15-oxo-12-prostenoic acid ethyl ester, dissolved in 200 ml. dry diethyl ether, with the exclusion of moisture, under nitrogen and with stirring. The mixture is stirred 30 minutes more at room temperature and mixed dropwise, with ice cooling, with 300 ml. saturated aqueous NH$_4$Cl solution. The organic phase is separated, washed with water and dried over Na$_2$SO$_4$. Solvent is removed to yield as residue, 9β,15-dihydroxy-15-ethyl-12-prostenoic acid ethyl ester.

The corresponding compounds of Formula III are treated with ethyl magnesium iodide to obtain:

9β,15-dihydroxy-15-ethyl-16-methyl-12-prostenoic acid ethyl ester;

9β,15-dihydroxy-15-ethyl-16,16-dimethyl-12-prostenoic acid ethyl ester;

9β,15-dihydroxy-15-ethyl-20-homo-12-prostenoic acid ethyl ester;

9β,15-dihydroxy-15-ethyl-16-methyl-20-homo-12-prostenoic acid ethyl ester;

9β,15-dihydroxy-15-ethyl-16,16-dimethyl-20-homo-12-prostenoic acid ethyl ester;

9β,15-dihydroxy-15-ethyl-20-bishomo-12-prostenoic acid ethyl ester;

9β,15-dihydroxy-15-ethyl-16-methyl-20-bishomo-12-prostenoic acid ethyl ester;

9β,15-dihydroxy-15-ethyl-16,16-dimethyl-20-bishomo-12-prostenoic acid ethyl ester;

9β,15-dihydroxy-17,18,19,20-tetranor-15-ethyl-16-phenoxy-12-prostenoic acid ethyl ester; and 9β,15-dihydroxy-17,18,19,20-tetranor-15-ethyl-16-p-fluorophenoxy-12-prostenoic acid ethyl ester.

EXAMPLE 18

The corresponding compounds of Formula III can be converted by reaction with propyl magnesium iodide in accordance with Example 17 to prepare:

9β,15-dihydroxy-15-propyl-12-prostenoic acid ethyl ester;

9β,15-dihydroxy-15-propyl-16-methyl-12-prostenoic acid ethyl ester;

9β,15-dihydroxy-15-propyl-16,16-dimethyl-12-prostenoic acid ethyl ester;

9β,15-dihydroxy-15-propyl-20-homo-12-prostenoic acid ethyl ester;

9β,15-dihydroxy-15-propyl-20-bishomo-12-prostenoic acid ethyl ester; and

9β,15-dihydroxy-17,18,19,20-tetranor-15-propyl-16-p-fluorophenoxy-12-prostenoic acid ethyl ester.

EXAMPLE 19

1.6 g. Butyl lithium, dissolved in 60 ml. tetrahydrofuran, is added dropwise to 3.7 g. 9β-hydroxy-15-oxo-12-prostenoic acid ethyl ester, dissolved in 150 ml. dry diethyl ether, with the exclusion of moisture, under argon and with stirring at −15°. The mixture is stirred for another hour, allowed to warm to 0° and mixed dropwise, with ice cooling, with 300 ml. saturated aqueous NH$_4$Cl solution. The organic phase is separated, washed with water and dried over Na$_2$SO$_4$. The solvent is removed to obtain as residue 9β,15-dihydroxy-15-butyl-12-prostenoic acid ethyl ester.

Compounds of Formula III react with butyl lithium to produce:

9β,15-dihydroxy-15-butyl-16-methyl-12-prostenoic acid ethyl ester;

9β,15-dihydroxy-15-butyl-16,16-dimethyl-12-prostenoic acid ethyl ester;

9β,15-dihydroxy-15-butyl-20-homo-12-prostenoic acid ethyl ester;

9β,15-dihydroxy-15-butyl-20-bishomo-12-prostenoic acid ethyl ester; and

9β,15-dihydroxy-17,18,19,20-tetranor-15-butyl-20-p-fluorophenoxy-12-prostenoic acid ethyl ester.

EXAMPLE 20

Compounds of Formula III react with pentyl lithium according to Example 19 to give:

9β,15-dihydroxy-15-pentyl-12-prostenoic acid ethyl ester;

9β,15-dihydroxy-15-pentyl-16-methyl-12-prostenoic acid ethyl ester;

9β,15-dihydroxy-15-pentyl-16,16-dimethyl-12-prostenoic acid ethyl ester;

9β,15-dihydroxy-15-pentyl-20-homo-12-prostenoic acid ethyl ester;

9β,15-dihydroxy-15-pentyl-20-bishomo-12-prostenoic acid ethyl ester;

9β,15-dihydroxy-17,18,19,20-tetranor-15-pentyl-16-phenoxy-12-prostenoic acid ethyl ester;

9β,15-dihydroxy-17,18,19,20-tetranor-15-pentyl-16-p-fluorophenoxy-12-prostenoic acid ethyl ester;

9β,15-dihydroxy-17,18,19,20-tetranor-15-pentyl-16-p-chlorophenoxy-12-prostenoic acid ethyl ester;

9β,15-dihydroxy-17,18,19,20-tetranor-15-pentyl-16-p-bromophenoxy-12-prostenoic acid ethyl ester;

9β,15-dihydroxy-17,18,19,20-tetranor-15-pentyl-16-p-methylphenoxy-12-prostenoic acid ethyl ester;

9β,15-dihydroxy-17,18,19,20-tetranor-15-pentyl-16-p-trifluoromethylphenoxy-12-prostenoic acid ethyl ester; and 9β,15-dihydroxy-17,18,19,20-tetranor-15-pentyl-16-p-methoxyphenoxy-12-prostenoic acid ethyl ester.

EXAMPLE 21

Following the procedure of Example 16, 9α-hydroxy-15-oxo-12-prostenoic acid ethyl ester is reacted with methyl magnesium bromide to produce 9α,15-dihydroxy-15-methyl-12-prostenoic acid ethyl ester as a mixture of the 15-epimers, $R_f$ = 0.29.

From the corresponding compounds of Formula III, by reaction with methyl magnesium iodide, there are obtainable:

9α,15-dihydroxy-15,16-dimethyl-12-prostenoic acid ethyl ester;
9α,15-dihydroxy-15,16,16-trimethyl-12-prostenoic acid ethyl ester;
9α,15-dihydroxy-15-methyl-20-homo-12-prostenoic acid ethyl ester;
9α,15-dihydroxy-15,16-dimethyl-20-homo-12-prostenoic acid ethyl ester;
9α,15-dihydroxy-15,16,16-trimethyl-20-homo-12-prostenoic acid ethyl ester;
9α,15-dihydroxy-15-methyl-20-bishomo-12-prostenoic acid ethyl ester;
9α,15-dihydroxy-15,16-dimethyl-20-bishomo-12-prostenoic acid ethyl ester;
9α,15-dihydroxy-15,16,16-trimethyl-20-bishomo-12-prostenoic acid ethyl ester;
9α,15-dihydroxy-17,18,19,20-tetranor-12-methyl-16-phenoxy-12-prostenoic acid ethyl ester;
9α,15-dihydroxy-17,18,19,20-tetranor-15-methyl-16-p-fluorophenoxy-12-prostenoic acid ethyl ester;
9α,15-dihydroxy-17,18,19,20-tetranor-15-methyl-16-p-chlorophenoxy-12-prostenoic acid ethyl ester;
9α,15-dihydroxy-17,18,19,20-tetranor-15-methyl-16-p-bromophenoxy-12-prostenoic acid ethyl ester;
9α,15-dihydroxy-17,18,19,20-tetranor-15-methyl-16-p-methylphenoxy-12-prostenoic acid ethyl ester;
9α,15-dihydroxy-17,18,19,20-tetranor-15-methyl-16-p-trifluoromethylphenoxy-12-prostenoic acid ethyl ester; and
9α,15-dihydroxy-17,18,19,20-tetranor-15-methyl-16-p-methoxyphenoxy-12-prostenoic acid ethyl ester.

EXAMPLE 22

Following the procedure of Example 17, compounds of Formula III can be reacted with ethyl magnesium iodide to obtain:

9α,15-dihydroxy-15-ethyl-12-prostenoic acid ethyl ester;
9α,15-dihydroxy-15-ethyl-16-methyl-12-prostenoic acid ethyl ester;
9α,15-dihydroxy-15-ethyl-16,16-dimethyl-12-prostenoic acid ethyl ester;
9α,15-dihydroxy-15-ethyl-20-homo-12-prostenoic acid ethyl ester;
9α,15-dihydroxy-15-ethyl-16-methyl-20-homo-12-prostenoic acid ethyl ester;
9α,15-dihydroxy-15-ethyl-16,16-dimethyl-20-homo-12-prostenoic acid ethyl ester;
9α,15-dihydroxy-15-ethyl-20-bishomo-12-prostenoic acid ethyl ester;
9α,15-dihydroxy-15-ethyl-16-methyl-20-bishomo-12-prostenoic acid ethyl ester;
9α,15-dihydroxy-15-ethyl-16,16-dimethyl-20-bishomo-12-prostenoic acid ethyl ester;
9α,15-dihydroxy-17,18,19,20-tetranor-15-ethyl-16-phenoxy-12-prostenoic acid ethyl ester; and
9α,15-dihydroxy-17,18,19,20-tetranor-15-ethyl-16-p-fluorophenoxy-12-prostenoic acid ethyl ester.

EXAMPLE 23

By the procedure of EXAMPLE 18, compounds of Formula III are treated with propyl magnesium iodide to obtain:

9α,15-dihydroxy-15-propyl-12-prostenoic acid ethyl ester;
9α,15-dihydroxy-15-propyl-16-methyl-12-prostenoic acid ethyl ester;
9α,15-dihydroxy-15-propyl-16,16-dimethyl-12-prostenoic acid ethyl ester;
9α,15-dihydroxy-15-propyl-20-homo-12-prostenoic acid ethyl ester;
9α,15-dihydroxy-15-propyl-20-bishomo-12-prostenoic acid ethyl ester; and
9α,15-dihydroxy-17,18,19,20-tetranor-12-propyl-16-p-fluorophenoxy-12-prostenoic acid ethyl ester.

EXAMPLE 24

By the procedure of Example 19, compounds of Formula III are treated with butyl lithium to obtain:

9α,15-dihydroxy-15-butyl-12-prostenoic acid ethyl ester;
9α,15-dihydroxy-15-butyl-16-methyl-12-prostenoic acid ethyl ester;
9α,15-dihydroxy-15-butyl-16,16-dimethyl-12-prostenoic acid ethyl ester;
9α,15-dihydroxy-15-butyl-20-homo-12-prostenoic acid ethyl ester;
9α,15-dihydroxy-15-butyl-20-bishomo-12-prostenoic acid ethyl ester; and
9α,15-dihydroxy-17,18,19,20-tetranor-15-butyl-16-p-fluorophenoxy-12-prostenoic acid ethyl ester.

EXAMPLE 25

In accordance with Example 19, compounds of Formula III and pentyl lithium react to yield:

9α,15-dihydroxy-15-pentyl-12-prostenoic acid ethyl ester;
9α,15-dihydroxy-15-pentyl-16-methyl-12-prostenoic acid ethyl ester;
9α,15-dihydroxy-15-pentyl-16,16,dimethyl-12-prostenoic acid ethyl ester;
9α,15-dihydroxy-15-pentyl-20-homo-12-prostenoic acid ethyl ester;
9α,15-dihydroxy-15-pentyl-20-bishomo-12-prostenoic acid ethyl ester;
9α,15-dihydroxy-17,18,19,20-tetranor-15-pentyl-15-phenoxy-12-prostenoic acid ethyl ester;
9α,15-dihydroxy-17,18,19,20-tetranor-15-pentyl-16-p-fluorophenoxy-12-prostenoic acid ethyl ester;
9α,15-dihydroxy-17,18,19,20-tetranor-15-pentyl-16-p-chlorophenoxy-12-prostenoic acid ethyl ester;
9α,15-dihydroxy-17,18,19,20-tetranor-15-pentyl-16-p-bromophenoxy-12-prostenoic acid ethyl ester;
9α,15-dihydroxy-17,18,19,20-tetranor-15-pentyl-16-p-methylphenoxy-12-prostenoic acid ethyl ester;
9α,15-dihydroxy-17,18,19,20-tetranor-15-pentyl-16-p-trifluoromethylphenoxy-12-prostenoic acid ethyl ester; and
9α,15-dihydroxy-17,18,19,20-tetranor-15-pentyl-16-p-methoxyphenoxy-12-prostenoic acid ethyl ester.

EXAMPLE 26

Pentyl magnesium bromide (prepared from 4.5 g. pentyl bromide and 0.72 g. magnesium filings) dissolved in 100 ml. dry diethyl ether is added dropwise to 3.1 g. 9β-hydroxy-15-oxo-17,18,19,20-tetranor-12-prostenoic acid ethyl ester, dissolved in 200 ml. dry diethyl ether, with the exclusion of moisture, under nitrogen and with stirring. The mixture is stirred 30 minutes more at room temperature and mixed by dropwise addition, with ice cooling, with 350 ml. saturated aqueous $NH_4Cl$ solution. The organic phase is separated, washed with water and dried over $Na_2SO_4$. The solvent is removed to obtain as residue 9β,15-dihydroxy-15-methyl-12-prostenoic acid ethyl ester which can be separated into the two 15-epimers by chromatographic purification (first silica gel/dichloromethane:acetone = 10:1, then silica gel/petroleum ether:ethanol = 9:1):

epimer A: $R_f = 0.20$
epimer B: $R_f = 0.27$.

Compounds of Formula V, by reaction with pentyl magnesium bromide, yield:

9α,15-dihydroxy-15-methyl-12-prostenoic acid ethyl ester, $R_f = 0.29$;
9β,15-dihydroxy-15-isopropyl-12-prostenoic acid ethyl ester;
9α,15-dihydroxy-15-isopropyl-12-prostenoic acid ethyl ester;
9β,15-dihydroxy-15-isobutyl-12-prostenoic acid ethyl ester;
9α,15-dihydroxy-15-isobutyl-12-prostenoic acid ethyl ester;
9β,15-dihydroxy-15-sec.-butyl-12-prostenoic acid ethyl ester; 9α,15-dihydroxy-15-sec.-butyl-12-prostenoic acid ethyl ester;
9β,15-dihydroxy-15-isopentyl-12-prostenoic acid ethyl ester;
9α,15-dihydroxy-15-isopentyl-12-prostenoic acid ethyl ester;
9β,15-dihydroxy-15-(1-methyl-butyl)-12-prostenoic acid ethyl ester;
9α,15-dihydroxy-15-(1-methyl-butyl)-12-prostenoic acid ethyl ester;
9β,15-dihydroxy-15-(2-methyl-butyl)-12-prostenoic acid ethyl ester;
9α,15-dihydroxy-15-(2-methyl-butyl)-12-prostenoic acid ethyl ester;
9β,15-dihydroxy-15-(1-ethyl-propyl)-12-prostenoic acid ethyl ester; and
9α,15-dihydroxy-15-(1-ethyl-propyl)-12-prostenoic acid ethyl ester.

EXAMPLE 27

A mixture of 100 mg. 9β,15-dihydroxy-12-prostenoic acid, 10 mg. p-toluenesulfonic acid and 2 ml. dry ethanol is allowed to stand overnight at room temperature with the exclusion of moisture, diluted with 20 ml. dichloromethane and washed twice with 10 ml. amounts of saturated aqueous NaCHO₃ solution. The organic phase is washed until neutral with three 10 ml. portions of water and dried over MgSO₄. The solvent is removed to obtain, as residue, 9β,15-dihydroxy-12-prostenoic acid ethyl ester which can be separated, as in Example 14, chromatographically into the two 15-epimers:

epimer A: $R_f = 0.27$
epimer B; $R_f = 0.22$.

EXAMPLE 28

Compounds of Formula VII are converted by hydrolysis according to Example 11 to:

9α,15-dihydroxy-12-prostenoic acid;
9α,15-dihydroxy-16-methyl-12-prostenoic acid;
9α,15-dihydroxy-16,16-dimethyl-12-prostenoic acid;
9α,15-dihydroxy-16-ethyl-12-prostenoic acid;
9α,15-dihydroxy-19,19-dimethyl-12-prostenoic acid;
9α,15-dihydroxy-20-homo-12-prostenoic acid;
9α,15-dihydroxy-16-methyl-20-homo-12-prostenoic acid;
9α,15-dihydroxy-16,16-dimethyl-20-homo-12-prostenoic acid;
9α,15-dihydroxy-20-bishomo-12-prostenoic acid;
9α,15-dihydroxy-16,16-dimethyl-20-bishomo-12-prostenoic acid;
9α,15-dihydroxy-16,16-dimethyl-20-bishomo-12-prostenoic acid;
9α,15-dihydroxy-17,18,19,20-tetranor-16-phenoxy-12-prostenoic acid;
9α,15-dihydroxy-17,18,19,20-tetranor-16-p-fluorophenoxy-12-prostenoic acid;
9α,15-dihydroxy-17,18,19,20-tetranor-16-p-chlorophenoxy-12-prostenoic acid;
9α,15-dihydroxy-17,18,19,20-tetranor-16-p-bromophenoxy-12-prostenoic acid;
9α,15-dihydroxy-17,18,19,20-tetranor-16-p-methylphenoxy-12-prostenoic acid;
9α,15-dihydroxy-17,18,19,20-tetranor-16-p-trifluoromethylphenoxy-12-prostenoic acid; and
9α,15-dihydroxy-17,18,19,20-tetranor-16-p-methoxyphenoxy-12-prostenoic acid.

EXAMPLE 29

A mixture of 250 mg. 9β,15-dihydroxy-15-methyl-12-prostenoic acid ethyl ester (as mixture of the two 15-epimers), 20 ml. 1,2-dimethoxyethane, 0.3 g. KOH and 5 ml. water is stirred for 12 hours at room temperature, diluted with 40 ml. diethyl ether and saturated with NaCl. The organic phase is separated, washed twice with 15 ml. amounts of H₂O and dried over MgSO₄. Solvent is removed to obtain, as oily residue, 9β,15-dihydroxy-15-methyl-12-prostenoic acid as mixture of the 15-epimers.

Alkaline hydrolysis of 12-prostenoic acid derivatives preparable according to Examples 16 and 21 yields:

9α,15-dihydroxy-15-methyl-12-prostenoic acid;
9β,15-dihydroxy-15,16-dimethyl-12-prostenoic acid;
9α,15-dihydroxy-15,16-dimethyl-12-prostenoic acid;
9β,15-dihydroxy-15,16,16-trimethyl-12-prostenoic acid;
9α,15-dihydroxy-15,16,16-trimethyl-12-prostenoic acid;
9β,15-dihydroxy-15-methyl-20-homo-12-prostenoic acid;
9α,15-dihydroxy-15-methyl-20-homo-12-prostenoic acid;
9β,15-dihydroxy-15,16-dimethyl-20-homo-12-prostenoic acid;
9α,15-dihydroxy-15,16-dimethyl-20-homo-12-prostenoic acid;
9β,15-dihydroxy-15,16,16-trimethyl-20-homo-12-prostenoic acid;
9α,15-dihydroxy-15,16,16-trimethyl-20-homo-12-prostenoic acid;
9β,15-dihydroxy-15-methyl-20-bishomo-12-prostenoic acid;
9α,15-dihydroxy-15-methyl-20-bishomo-12-prostenoic acid;
9β,15-dihydroxy-15,16-dimethyl-20-bishomo-12-prostenoic acid;
9α,15-dihydroxy-15,16-dimethyl-20-bishomo-12-prostenoic acid;
9β,15-dihydroxy-15,16,16-trimethyl-20-bishomo-12-prostenoic acid;
9α,15-dihydroxy-15,16,16-trimethyl-20-bishomo-12-prostenoic acid;
9β,15-dihydroxy-17,18,18,20-tetranor-15-methyl-16-phenoxy-12-prostenoic acid;
9α,15-dihydroxy-17,18,19,20-tetranor-15-methyl-16-phenoxy-12-prostenoic acid;

9β,15-dihydroxy-17,18,19,20-tetranor-15-methyl-16-p-fluorophenoxy-12-prostenoic acid; and
9α,15-dihydroxy-17,18,19,20-tetranor-15-methyl-16-p-fluorophenoxy-12-prostenoic acid.

EXAMPLE 30

Following the procedure of Example 29, alkaline hydrolysis of the 12-prostenoic acid derivatives, preparable according to Examples 17 and 22, produces:
9α,15-dihydroxy-15-ethyl-12-prostenoic acid;
9β,15-dihydroxy-15-ethyl-12-prostenoic acid;
9α,15-dihydroxy-15-ethyl-16-methyl-12-prostenoic acid;
9β,15-dihydroxy-15-ethyl-16-methyl-12-prostenoic acid;
9α,15-dihydroxy-15-ethyl-16,16-dimethyl-12-prostenoic acid;
9β,15-dihydroxy-15-ethyl-16,16-dimethyl-12-prostenoic acid;
9α,15-dihydroxy-15-ethyl-20-homo-12-prostenoic acid;
9β,15-dihydroxy-15-ethyl-20-homo-12-prostenoic acid;
9α,15-dihydroxy-15-ethyl-20-bishomo-12-prostenoic acid;
9β,15-dihydroxy-15-ethyl-20-bishomo-12-prostenoic acid;
9α,15-dihydroxy-17,18,19,20-tetranor-16-p-fluorophenoxy-12-prostenoic acid; and
9β,15-dihydroxy-17,18,19,20-tetranor-15-ethyl-16-p-fluorophenoxy-12-prostenoic acid.

EXAMPLE 31

The 12-prostenoic acid derivatives preparable according to Examples 18, 19, 20, 23, 24 and 25 are converted, according to Example 29, to:
9α,15-dihydroxy-15-propyl-12-prostenoic acid;
9β,15-dihydroxy-15-propyl-12-prostenoic acid;
9α,15-dihydroxy-15-propyl-16-methyl-12-prostenoic acid;
9β,15-dihydroxy-15-propyl-16-methyl-12-prostenoic acid;
9α,15-dihydroxy-15-propyl-16,16-dimethyl-12-prostenoic acid;
9β,15-dihydroxy-15-propyl-16,16-dimethyl-12-prostenoic acid;
9α,15-dihydroxy-15-propyl-20-homo-12-prostenoic acid;
9α,15-dihydroxy-15-propyl-20-bishomo-12-prostenoic acid;
9β,15-dihydroxy-15-propyl-20-bishomo-12-prostenoic acid; 9α,15-dihydroxy-17,18,19,20-tetranor-15-propyl-16-p-fluorophenoxy-12-prostenoic acid;
9β,15-dihydroxy-17,18,19,20-tetranor-15-propyl-16-p-fluorophenoxy-12-prostenoic acid;
9α,15-dihydroxy-15-butyl-12-prostenoic acid;
9β,15-dihydroxy-15-butyl-12-prostenoic acid;
9α,15-dihydroxy-15-butyl-16-methyl-12-prostenoic acid;
9β,15-dihydroxy-15-butyl-16-methyl-12-prostenoic acid;
9α,15-dihydroxy-15-butyl-16,16-dimethyl-12-prostenoic acid;
9β,15-dihydroxy-15-butyl-16,16-dimethyl-12-prostenoic acid;
9α,15-dihydroxy-15-butyl-20-homo-12-prostenoic acid;
9β,15-dihydroxy-15-butyl-20-homo-12-prostenoic acid;
9α,15-dihydroxy-15-butyl-20-bishomo-12-prostenoic acid;
9β,15-dihydroxy-15-butyl-20-bishomo-12-prostenoic acid;
9α,15-dihydroxy-17,18,19,20-tetranor-15-butyl-16-p-fluorophenoxy-12-prostenoic acid;
9β,15-dihydroxy-17,18,19,20-tetranor-15-butyl-16-p-fluorophenoxy-12-prostenoic acid;
9α,15-dihydroxy-15-pentyl-12-prostenoic acid;
9β,15-dihydroxy-15-pentyl-12-prostenoic acid;
9α,15-dihydroxy-15-pentyl-16-methyl-12-prostenoic acid;
9β,15-dihydroxy-15-pentyl-16-methyl-12-prostenoic acid;
9α,15-dihydroxy-15-pentyl-16,16-dimethyl-12-prostenoic acid;
9β,15-dihydroxy-15-pentyl-16,16-dimethyl-12-prostenoic acid;
9α,15-dihydroxy-15-pentyl-20-homo-12-prostenoic acid;
9β,15-dihydroxy-15-pentyl-20-homo-12-prostenoic acid;
9α,15-dihydroxy-15-pentyl-20-bishomo-12-prostenoic acid;
9β,15-dihydroxy-15-pentyl-20-bishomo-12-prostenoic acid;
9α,15-dihydroxy-17,18,19,20-tetranor-15-pentyl-16-p-fluorophenoxy-12-prostenoic acid; and
9β,15-dihydroxy-17,18,19,20-tetranor-15-pentyl-16-p-fluorophenoxy-12-prostenoic acid.

The following Examples concern pharmaceutical compositions containing prostanoic acid derivatives of Formula I or their pharmacologically compatible and physiologically acceptable salts:

EXAMPLE A: Tablets

A mixture consisting of 30 g. of the sodium salt of 9β,15-dihydroxy-15-methyl-12-prostenoic acid, 50 g. lactose, 16 g. maize starch, 2 g. cellulose powder and 2 g. magnesium stearate is pressed into tablets in the usual way so that each tablet contains 30 mg. of active material.

EXAMPLE B: Dragees

Tablets pressed according to Example A are subsequently coated in the usual way with a coating consisting of sugar, maize starch, talc and tragacanth.

Tablets and dragees containing one or more of the other active materials of Formula I or of their physiologically acceptable acid-addition salts, are obtainable similarly.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A prostenoic acid derivative of the formula

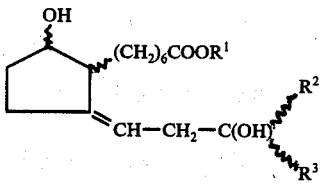

wherein,
R¹ is H or alkyl of 1 to 4 carbon atoms;
R² is alkyl of 5 to 9 carbon atoms;
R³ is H or alkyl of 1 to 5 carbon atoms; and physiologically acceptable salts thereof.

2. A compound of claim 1, wherein R¹ is H.
3. A compound of claim 1, wherein R¹ is methyl or ethyl.
4. A compound of claim 1, wherein R² is pentyl.
5. A compound of claim 1, wherein R² is 1-methylpentyl.
6. A compound of claim 1, wherein R² is 1,1-dimethylpentyl.
7. A compound of claim 1, wherein the 9-hydroxy group is α.
8. A compound of claim 1, wherein R³ is H.
9. A compound of claim 1, wherein R³ is methyl or ethyl.
10. A compound of claim 1, wherein R¹ is H and R² is pentyl.
11. A compound of claim 1, wherein R¹ is H and R³ is H or methyl.
12. A compound of claim 1, wherein R¹ is methyl or ethyl and R³ is H or methyl.
13. A compound of claim 1, wherein R¹ is H or ethyl, R² is pentyl, 1-methylpentyl or 1,1-dimethylpentyl and R³ is H or methyl.
14. A compound of claim 1, wherein the 9-hydroxy group is β.
15. 9α,15-Dihydroxy-12-prostenoic acid, a compound of claim 1.
16. 9α,15-Dihydroxy-15-methyl-12-prostenoic acid, a compound of claim 1.
17. 9α,15-Dihydroxy-16-methyl-12-prostenoic acid, a compound of claim 1.
18. 9α,15-Dihydroxy-15-pentyl-12-prostenoic acid, a compound of claim 1.
19. 9α,15-Dihydroxy-15,16-dimethyl-12-prostenoic acid, a compound of claim 1.
20. 9α,15-Dihydroxy-16,16-dimethyl-12-prostenoic acid, a compound of claim 1.
21. 9α,15-Dihydroxy-15,16,16-trimethyl-12-prostenoic acid, a compound of claim 1.
22. 9α,15-Dihydroxy-20-homo-12-prostenoic acid, a compound of claim 1.
23. 9α,15-Dihydroxy-20-bishomo-12-prostenoic acid, a compound of claim 1.
24. 9α,15-Dihydroxy-15,16,16-trimethyl-12-prostenoic acid ethyl ester, a compound of claim 1.
25. 9α,15-Dihydroxy-15-pentyl-12-prostenoic acid ethyl ester, a compound of claim 1.
26. 9α,15-Dihydroxy-15,16-dimethyl-12-prostenoic acid ethyl ester, a compound of claim 1.
27. 9α,15-Dihydroxy-12-prostenoic acid ethyl ester, a compound of claim 1.
28. 9α,15-Dihydroxy-15-methyl-12-prostenoic acid methyl ester, a compound of claim 1.
29. 9α,15-Dihydroxy-16-methyl-12-prostenoic acid ethyl ester, a compound of claim 1.
30. 9α,15-Dihydroxy-16,16-dimethyl-12-prostenoic acid ethyl ester, a compound of claim 1.
31. 9α,15-Dihydroxy-20-homo-12-prostenoic acid ethyl ester, a compound of claim 1.
32. 9α,15-Dihydroxy-20-bishomo-12-prostenoic acid ethyl ester, a compound of claim 1.
33. 9β,15-Dihydroxy-12-prostenoic acid, a compound of claim 1.
34. 9β,15-Dihydroxy-15-methyl-12-prostenoic acid, a compound of claim 1.
35. 9β,15-Dihydroxy-16-methyl-12-prostenoic acid, a compound of claim 1.
36. 9β,15-Dihydroxy-15-pentyl-12-prostenoic acid, a compound of claim 1.
37. 9β,15-Dihydroxy-15,16-dimethyl-12-prostenoic acid, a compound of claim 1.
38. 9β,15-Dihydroxy-16,16-dimethyl-12-prostenoic acid, a compound of claim 1.
39. 9β,15-Dihydroxy-15,16,16-trimethyl-12-prostenoic acid, a compound of claim 1.
40. 9β,15-Dihydroxy-20-homo-12-prostenoic acid, a compound of claim 1.
41. 9β,15-Dihydroxy-20-bishomo-12-prostenoic acid, a compound of claim 1.
42. 9β,15-Dihydroxy-15-pentyl-12-prostenoic acid ethyl ester, a compound of claim 1.
43. 9β,15-Dihydroxy-15,16-dimethyl-12-prostenoic acid ethyl ester, a compound of claim 1.
44. 9β,15-Dihydroxy-15,16,16-trimethyl-12-prostenoic acid ethyl ester, a compound of claim 1.
45. 9β,15-Dihydroxy-12-prostenoic acid ethyl ester, a compound of claim 1.
46. 9β,15-Dihydroxy-15-methyl-12-prostenoic acid ethyl ester, a compound of claim 1.
47. 9β,15-Dihydroxy-16-methyl-12-prostenoic acid ethyl ester, a compound of claim 1.
48. 9β,15-Dihydroxy-16,16-methyl-12-prostenoic acid ethyl ester, a compound of claim 1.
49. 9β,15-Dihydroxy-20-homo-12-prostenoic acid ethyl ester, a compound of claim 1.
50. 9β,15-Dihydroxy-20-bishomo-12-prostenoic acid ethyl ester, a compound of claim 1.
51. 9α,15-Dihydroxy-15-methyl-12-prostenoic acid ethyl ester, a compound of claim 1.
52. A pharmaceutical composition comprising an amount per unit dosage of a compound of claim 1 effective to alleviate the symptoms of hypertension, in admixture with a pharmaceutically acceptable carrier.

* * * * *